(12) United States Patent
Jackwood et al.

(10) Patent No.: US 11,814,653 B2
(45) Date of Patent: Nov. 14, 2023

(54) ATTENUATED ISOLATE OF INFECTIOUS BRONCHITIS VIRUS STRAIN DMV1639

(71) Applicant: UNIVERSITY OF GEORGIA RESEARCH FOUNDATION, INC., Athens, GA (US)

(72) Inventors: Mark W. Jackwood, Watkinsville, GA (US); Brian J. Jordan, Madison, GA (US)

(73) Assignee: UNIVERSITY OF GEORGIA RESEARCH FOUNDATION, INC., Athens, GA (US)

( * ) Notice: Subject to any disclaimer, the term of this patent is extended or adjusted under 35 U.S.C. 154(b) by 121 days.

(21) Appl. No.: 17/481,411

(22) Filed: Sep. 22, 2021

(65) Prior Publication Data

US 2022/0090024 A1    Mar. 24, 2022

Related U.S. Application Data

(60) Provisional application No. 63/081,392, filed on Sep. 22, 2020.

(51) Int. Cl.
  *C12N 7/00* (2006.01)
  *A61K 39/215* (2006.01)
  *A61K 39/00* (2006.01)

(52) U.S. Cl.
  CPC .............. *C12N 7/00* (2013.01); *A61K 39/215* (2013.01); *A61K 2039/5254* (2013.01); *A61K 2039/552* (2013.01); *C12N 2770/20034* (2013.01)

(58) Field of Classification Search
  None
  See application file for complete search history.

(56) References Cited

U.S. PATENT DOCUMENTS

| 9,809,802 | B2 * | 11/2017 | Solano ................ A61K 39/12 |
| 10,329,538 | B2 | 6/2019 | Jordan et al. |
| 11,441,127 | B2 | 9/2022 | Jordan et al. |
| 2016/0032253 | A1 * | 2/2016 | Sellers ................ C07K 14/005 |
| | | | 435/320.1 |
| 2016/0256554 | A1 * | 9/2016 | Genin ................ A61K 9/2013 |
| 2018/0066236 | A1 | 3/2018 | Solano et al. |
| 2018/0216082 | A1 | 8/2018 | Jordan et al. |
| 2019/0264180 | A1 | 8/2019 | Jordan et al. |
| 2022/0090024 | A1 * | 3/2022 | Jackwood ............ A61K 39/215 |

FOREIGN PATENT DOCUMENTS

| WO | 2018/140714 A1 | 8/2018 |
| WO | 2022/066683 A1 | 3/2022 |

OTHER PUBLICATIONS

Hassan et al. (Viruses. 2019; 11: 1054).*
Jackwood and Lee (PLoSOne. May 2017; 12(5): e0176709).*
(Continued)

*Primary Examiner* — Shanon A. Foley
(74) *Attorney, Agent, or Firm* — Mueting Raasch Group

(57) ABSTRACT

A heat attenuated infectious bronchitis virus (IBV) isolate of PDRC DMV/1639 deposited at the ATCC under Patent Designation PTA-126757 and progeny and derivatives thereof and compositions thereof are presented. Methods for administering the isolates and compositions as vaccines to prevent virulent IBV infection in birds of the order Galliformes are also presented.

19 Claims, 12 Drawing Sheets

(56) References Cited

OTHER PUBLICATIONS

Gelb et al. (Avian Diseases. 2013; 57(1): 65-70).*
Valastro et al., S1 gene-based phylogeny of infectious bronchitis virus: An attempt to harmonize virus classification. Infect Genet Evol 39, 349-364 (2016).
Reed et al., A Simple Method of Estimating Fifty Per Cent Endpoints. American Journal of Hygiene, 27, 493-497 (1938).
Masters, The molecular biology of coronaviruses. Adv Virus Res 66, 193-292 (2006).
Lohr, Diagnosis of infectious bronchitis (IB) by examination of tracheal mucus for IB-precipitating antigens. Avian Dis 25, 1058-1064 (1981).
Lohr, Infectious bronchitis agar-gel precipitin test—use of infected allantoic fluid as antigen. Avian Dis 24, 463-467 (1980).
Lashgari et al., Serological comparison and antigenic relationships of seven serotypes of infectious bronchitis virus using the hemagglutination-inhibition test. Avian Dis 28, 435-443 (1984).
Kwon et al., Differentiation of infectious bronchitis virus serotypes using polymerase chain reaction and restriction fragment length polymorphism analysis. Avian Dis 37, 194-202 (1993).
King et al., Evaluation of the hemagglutination-inhibition test for measuring the response of chickens to avian infectious bronchitis virus vaccination. Avian Dis 27, 100-112 (1983).
Jackwood et al., Evaluating Protection Against Infectious Bronchitis Virus by Clinical Signs, Ciliostasis, Challenge Virus Detection, and Histopathology. Avian Dis 59, 368-374 (2015).
Jackwood et al., Rapid heat-treatment attenuation of infectious bronchitis virus. Avian Pathol 39, 227-233 (2010).
Cavanagh, Coronavirus avian infectious bronchitis virus. Vet Res 38, 281-297 (2007).
Cavanagh, Severe acute respiratory syndrome vaccine development: experiences of vaccination against avian infectious bronchitis coronavirus. Avian Pathol 32, 567-582 (2003).
Callison et al., Development and evaluation of a real-time Taqman RT-PCR assay for the detection of infectious bronchitis virus from infected chickens. J Virol Methods 138, 60-65 (2006).
Stayer, Infectious bronchitis DMV 1639: More questions than answers, retrieved on Jul. 24, 2020, retrieved from poultryhealthtoday.com, 3 pages (2020).
thepoultrysite.com [online], "DMV/1639 now the focus of many IBV control programs in US flocks", Poultry Health Today, retrieved on Jul. 24, 2020, retrieved from URL: thepoultrysite.com/news/2020/04/dmv-1639-now-the-focus-of-many-ibv-control-programs-in-us-flocks, 3 pages (2020).
Jackwood et al., Different evolutionary trajectories of vaccine-controlled and non-controlled avian infectious bronchitis viruses in commercial poultry. PLoS One 12(5): e0176709 (2017).
Hassan et al., Delmarva (DMV/1639) Infectious Bronchitis Virus (IBV) Variants Isolated in Eastern Canada Show Evidence of Recombination. Viruses 11, 105, 16 pages (2019).
Goraichuk et al., First Complete Genome Sequence of Currently Circulating Infectious Bronchitis Virus Strain DMV/1639 of the GI-17 Lineage. Microbiology Resource Announcements 8(34):e00840-19 (2019).
Schaeffer, Infectious Bronchitis: Evolving Strategies for an Evolving Virus, Poultry Health Today: Highlights of a Roundtable Discussion, 28 pages (2020).
PCT Patent Application No. PCT/US2021/051413, filed Sep. 22, 2021, International Search Report and Written Opinion dated Dec. 27, 2021, 8 pages.
PCT Patent Application No. PCT/US2021/051413, filed Sep. 22, 2021, International Preliminary Report on Patentability dated Mar. 28, 2023, 6 pages.
Gelb et al., Characterization of nephropathogenic infectious bronchitis virus DMV/1639/11 recovered from Delmarva broiler chickens in 2011, Avian Dis, 57(1):65-70 (2013).
Dufour-Zavala, A laboratory manual for the isolation, identification and characterization of avian pathogens, American Association of Avian Pathologists (2008).
uspoultry.org [online], "Economic Data, in U.S. Poultry & Egg Association", retrieved on Apr. 30, 2023, retrieved from URL: uspoultry.org/economic-data/, 2 pages (2016).
Jackwood et al., Review of Infectious Bronchitis Virus Around the World, Avian Diseases, 56(4):634-641 (2012).
Jordan, Spray Cabinet Application of Infectious Bronchitis Virus Vaccines in the Hatchery: How Efficient Are We?, Dept. of Population Health, University of Georgia, Issue 134, 4 pages (2015).
govinfo.gov [online], § 113.327 Bronchitis Vaccine, believed to be available as early as Jan. 1, 2011, retrieved on Apr. 30, 2023, retrieved from URL: govinfo.gov/content/pkg/CFR-2011-title9-vol1/pdf/CFR-2011-title9-vol1-sec113-327.pdf, 9 CFR Ch. 1, Jan. 1, 2011 Edition, 3 pages.
Jordan, Vaccination against infectious bronchitis virus: A continuous challenge, Veterinary Microbiology, 206, 137-143 (2017).

* cited by examiner

FIG. 9

Post Challenge Clinical Signs

Bar chart showing Clinical Sign Score (0.0 to 3.0) for groups: -/-, DE1639/-, PDRC DMV/1639/-, DE1639/DMV, PDRC DMV/1639/DMV, -/DMV. Asterisks (*) indicate significance between -/- through DE1639/DMV and between PDRC DMV/1639/DMV and -/DMV.

ATTENUATED ISOLATE OF INFECTIOUS BRONCHITIS VIRUS STRAIN DMV1639

CONTINUING APPLICATION DATA

This application claims the benefit of U.S. Provisional Application Ser. No. 63/081,392, filed Sep. 22, 2020, which is incorporated by reference herein.

BACKGROUND

Avian infectious bronchitis virus (IBV) causes an economically significant upper respiratory tract disease in chickens (Economic Data, in U.S. Poultry & Egg Association, 2016). Because of its prevalence and infectivity, nearly all commercial poultry in the U.S. are vaccinated against IBV in a serotype-specific manner (Cavanagh *Vet Res* 38, 281-297 (2007)). IBV is an enveloped, positive-sense single-stranded ribonucleic acid (RNA) virus which belongs to the genus Gammacoronavirus of the family Coronaviridae. Like most RNA viruses, IBV is genetically diverse, due to a high mutation rate and recombination events. New IBV variants are continuously emerging, which complicates vaccination-based infectious bronchitis (IB) control. The Delmarva/1639 (DMV/1639) strain of IBV was first isolated from an IB outbreak in the Delaware/Maryland/Virginia (DELMARVA) peninsula, United States of America, in 2011 (Gelb et al. *Avian Dis* 57, 65-70 (2013)). It is currently a significant economic problem in the poultry industry and continues to spread. And, while cross-protection against the DMV/1639 strain by vaccination with one or more other IBV serotypes may be partially effective in limiting the clinical signs associated with DMV/1639 infection, there is a need for improved vaccines against DMV/1639 type viruses.

SUMMARY OF THE INVENTION

The present invention includes an infectious bronchitis virus (IBV) isolate, wherein the IBV isolate includes the heat attenuated IBV isolate PDRC DMV/1639 deposited at the ATCC under Patent Designation PTA-126757 or a progeny or derivative thereof, wherein a progeny or derivative thereof has essentially the same biological and serological characteristics of the heat attenuated IBV isolate PDRC DMV/1639 deposited at the ATCC under Patent Designation PTA-126757. In some aspects, the IBV isolate is lyophilized, freeze dried, or frozen.

The present invention also includes compositions including an IBV isolate or a progeny or derivative as described herein. In some aspects, the composition further includes a pharmaceutically acceptable carrier. In some aspects, the composition further includes an adjuvant. In some aspects, the composition further includes other viral material. In some aspects, the composition is formulated for intranasal, intraocular, oral, mucosal, intramuscular, subcutaneous, or in ovo administration. In some aspects, the composition is formulated for spraying or aerosolizing.

The present invention also includes vaccines including an IBV isolate or a progeny or derivative thereof as described herein or a composition as described herein. In some aspects, the vaccine reduces one or more of the clinical signs and/or the viral load induced by an IBV infection in poultry.

The present invention includes a vaccine for birds of the order Galliformes, the vaccine including an amount of the heat attenuated IBV isolate PDRC DMV/1639 deposited at the ATCC under Patent Designation PTA-126757, or a progeny or derivative thereof, sufficient to protect the birds from one or more clinical signs induced by an infectious bronchitis virus (IBV) infection in poultry.

The present invention also includes an effervescent tablet including an IBV isolate or a progeny or derivative, a composition, or a vaccine as described herein.

The present invention also includes methods of producing an immune response to an infectious bronchitis virus (IBV) in poultry, the method including administering an IBV isolate or a progeny or derivative, a composition, or a vaccine as described herein.

The present invention also includes methods of producing anti-IBV antibodies in poultry, the method including administering an IBV isolate or a progeny or derivative thereof, a composition, or a vaccine as described herein to the poultry.

The present invention also includes methods of reducing one or more clinical signs and/or viral load induced by an infectious bronchitis virus (IBV) infection in poultry, the method including administering an effective amount of an IBV isolate or a progeny or derivative thereof, a composition, or a vaccine as described herein.

The present invention also includes methods for reducing susceptibility of a bird of the order Galliformes against infectious bronchitis virus (IBV) infection, the method including administering to the bird an effective amount of an IBV isolate or a progeny or derivative thereof, a composition, or a vaccine as described herein.

The present invention also includes methods for protecting a bird of the order Galliformes against infectious bronchitis virus (IBV) infection, the method including administering to the bird an effective amount of an IBV isolate or a progeny or derivative, a composition, or a vaccine as described herein.

In some aspects, with a method described herein, administration is intranasal, intraocular, oral, mucosal, intramuscular, or subcutaneous.

In some aspects, with a method described herein, administration includes in ovo administration.

In some aspects, with a method described herein, the IBV isolate or a progeny or derivative thereof, composition, or vaccine is administered by aerosol.

In some aspects, with a method described herein, the IBV isolate or a progeny or derivative, composition, or vaccine is administered by spraying.

In some aspects, with a method described herein, the IBV isolate or a progeny or derivative, composition, or vaccine is administered by drinking water.

In some aspects, with a method described herein, administration includes administration to a breeder hen.

In some aspects, with a method described herein, poultry includes a bird of the order Galliformes.

In some aspects, with a method described herein, the bird is a chicken or turkey.

BRIEF DESCRIPTION OF THE FIGURES

FIG. 1A shows viral load (Inverted Ct Value) and percent positive for vaccination with De1639, PDRC DMV1639, and MA DMV/1639+Mass. FIG. 1B shows viral load and percent positive for vaccination with DE1639+iBron, iBron, and iBron+Mass.

FIG. 3A shows inverted Ct values. FIG. 3B shows percent positive.

FIG. 9. Post challenge clinical signs by vaccine/challenge group.

DETAILED DESCRIPTION

Figure 1A:
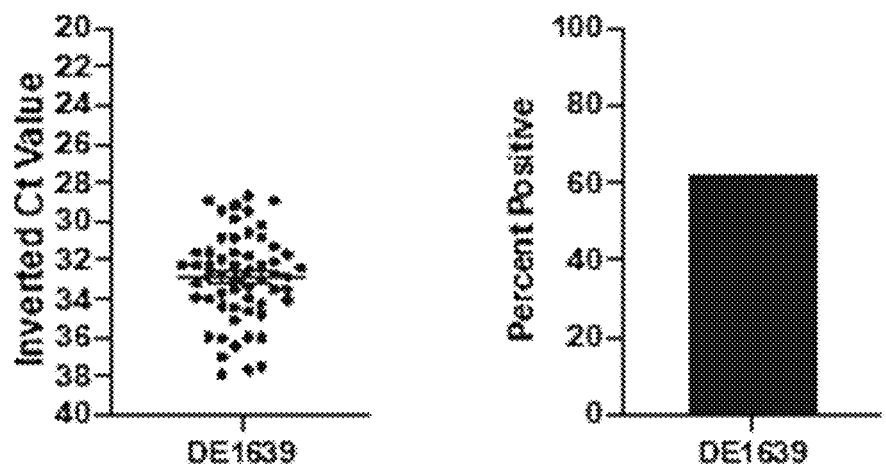
FIGS. 1A and 1B. Seven day takes post vaccination.
Figure 1A:
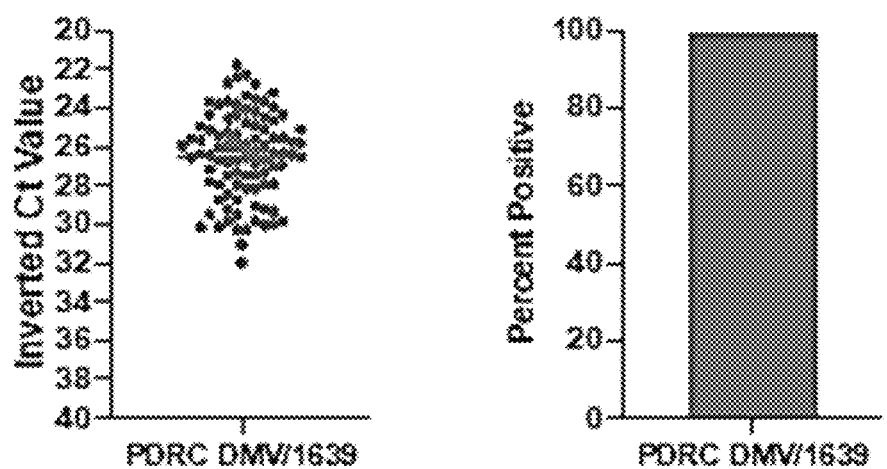
Figure 1A:
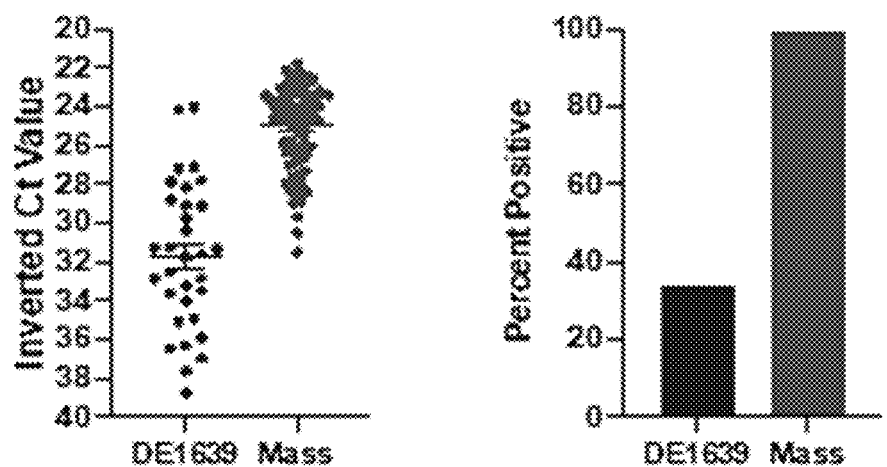

The present invention relates to new materials and methods in the field of poultry virology, particularly in the field of the infectious bronchitis virus (IBV).

Avian infectious bronchitis virus (IBV) is a gammacoronavirus. The enveloped IBV virus has a single stranded-positive sense RNA genome that codes for the viral RNA-dependent RNA-polymerase, three major structural proteins (the nucleocapsid, membrane, and spike (S) proteins), and numerous regulatory proteins (Masters Adv Virus Res 66, 193-292 (2006)). The spike glycoprotein of IBV is translated as a precursor protein (So) and then cleaved into two subunits, the N-terminal S1 glycoprotein and the C-terminal S2 glycoprotein by host cell serine proteases. The S1 and S2 glycoproteins mediate cell attachment, virus-cell membrane fusion, and play an important role in host cell specificity, forming club shaped projections on the surface of the virus. The S1 glycoprotein induces virus-neutralizing and hemagglutination-inhibiting antibodies.

New variant strains arise due to rapid recombination, insertions, deletions, or point mutation events, predominantly in the S1 spike protein gene. Along with the use of serologic based tests, PCR, and partial sequencing of the S1 gene can be used to group and type IBV isolates. A few changes in the sequence of the spike glycoprotein can result in a new serotype. It has been documented that as little as a 5% difference in the S1 sequence of IBV can result in a loss of cross-protection between otherwise similar isolates (Cavanagh *Avian Pathol* 32, 567-582 (2003)). Based on the spike 1 (S1) protein variability, six genotypes of IBV comprising 32 distinct viral lineages have been described (Valastro et al. *Infect Genet Evol* 39, 349-364 (2016)) have been recognized worldwide.

The Delmarva/1639 (DMV/1639) strain of IBV was first isolated from an infectious bronchitis (IB) outbreak in the Delmarva peninsula in 2011 (Gelb et al. *Avian Dis* 57, 65-70 (2013)) and infections with this IBV variant present a continuing challenge for poultry producers. Currently there is no commercial vaccine for this strain of IBV. And, while cross-protection against the DMV/1639 strain by vaccination with one or more other IBV serotypes may prove effective in limiting the mortality and morbidity associated with DMV/1639 infection, there is a need for improved vaccines against DMV/1639 type viruses.

The present invention provides a live, heat attenuated isolate of IBV strain DMV1639, and progeny and derivatives thereof. When administered to birds as a live formulation this attenuated IBV isolate is safe and efficacious in preventing IBV infections and reducing the incidence and severity of IBV infections.

This live, heat attenuated isolate of the IBV strain DMV1639 (also referred to herein as heat attenuated DMV/1639, attenuated DMV/1639, PDRC DMV/1639, heat attenuated PDRC DMV1639, and Attenuated DMV/1639—Georgia Isolate was deposited with the American Type Culture Collection (ATCC®) Patent Depository, 10801 University Boulevard, Manassas, Virginia 20110-2209, USA on May 15, 2020, as Patent Deposit Number PTA-126757. Such a deposit is in accordance with the Budapest Treaty on the International Recognition of the Deposit of Microorganisms for the Purposes of Patent Procedure.

Also included in the present invention are isolated progeny and isolated derivatives of the live, heat attenuated isolate of the IBV strain DMV1639 deposited with the ATCC® as Patent Deposit Number PTA-126757 on May 15, 2020, with equivalent or similar biological, serological, and/or genetic characteristics. As used herein, serological, biological, and genetic characteristics may include one or more of the characteristics described in the data in the Examples included herewith. More particularly, progeny or derivative strains of PTA-126757 may retain the particularly favorable protective properties belonging to the present invention, as described in more detail in the examples included herewith.

An IBV viral isolate according to the invention can be propagated by conventional methods, including, but not limited to, any of those described in the examples section included herewith. In brief, a substrate able to support the replication of an IBV virus isolate is inoculated with an IBV viral isolate of the present invention and propagated until the virus is replicated to a desired infectious titer, or antigen mass content. Virus containing material is then harvested. Suitable substrates may include embryonated eggs, primary (avian) cell cultures, such as, for example, chicken embryo liver cells, chicken embryo fibroblasts, or chicken kidney cells, mammalian cell lines, such as, for example, the VERO cell line or the BGM-70 cell line, or avian cell lines, such as, for example, QT-35, QM-7 or LMH.

In preferred embodiments, the virus may be propagated in embryonated eggs, including, but not limited to embryonated chicken eggs. For example, 9-to-11-day-old embryonated chicken eggs may be inoculated via the chorioallantoic sac (CAS) route (Dufour-Zavala, "A laboratory manual for the isolation, identification and characterization of avian pathogens," 5th ed. American Association of Avian Pathologists, Jacksonville, Fl. 2008. Inoculated eggs may be incubated at 37° C. for 48 hours, at which point the chorioallantoic fluid is collected.

Compositions and vaccines of the present invention may have titer of about $10^{1.5}$ to about $10^{10}$ $EID_{50}$ (embryo infective dose)/ml. In some aspects, a composition or vaccine of the present invention may have a titer about $10^{1.5}$ $EID_{50}$/ml, about $10^{2}$ $EID_{50}$/ml, about $10^{2.5}$ $EID_{50}$/ml, about $10^{3}$ $EID_{50}$/ml, about $10^{3.5}$ $EID_{50}$/ml, about $10^{4}$ $EID_{50}$/ml, about $10^{4.5}$ $EID_{50}$/ml, about $10^{5}$ $EID_{50}$/ml, about $10^{5.5}$ $EID_{50}$/ml, about $10^{6}$ $EID_{50}$/ml, about $10^{6.5}$ $EID_{50}$/ml, about $10^{7}$ $EID_{50}$/ml, about $10^{7.5}$ $EID_{50}$/ml, about $10^{8}$ $EID_{50}$/ml, about $10^{8.5}$ $EID_{50}$/ml, about $10^{9}$ $EID_{50}$/ml, about $10^{9.5}$ $EID_{50}$/ml, about $10^{10}$ $EID_{50}$/ml, or any range thereof. For example, in some applications a composition or vaccine of the present invention may have a titer about $10^{2}$ $EID_{50}$/ml to about $10^{8}$ $EID_{50}$/ml. Titers may be measured, for example in allantoic fluid.

Viruses may be titrated, for example, using the following protocol: 10-fold serial dilutions of the virus are made in sterile deionized water and each dilution inoculated into five 10-day-old embryonated SPF chicken eggs (0.1 ml/egg). Inoculated eggs are incubated at 37° C. for 7-days and embryos are examined for IBV-specific lesions. Embryo mortality within 24-hours post-inoculation is considered nonspecific and not included in virus titer calculations. Virus titers are calculated by the method of Reed and Muench (REED et al. *American Journal of Epidemiology* 27, 493-497 (1938)) and expressed as the 50% embryo infectious dose ($EID_{50}$).

The present invention includes compositions and vaccines including an isolated virus as described herein. In some applications vaccine preparations of the present invention may be prepared and tested according to Section 113.327 of Title 9 of the Code of Federal Regulations (CFR) for IBV vaccine testing.

In some embodiments, the virus is live. In some embodiments, the virus is inactivated or killed. Viruses and compositions and vaccines thereof of the present invention may be stored until use in any of a variety of forms. For example, such materials, may be lyophilized or freeze dried and may be rehydrated for use. In some embodiments, a virus or composition or vaccine thereof may be frozen.

In some embodiments, a virus, composition, or vaccine thereof may be formulated as an effervescent table. Such effervescent tablets may, for example, be packaged in light-weight aluminum blisters. The table may be dissolved in water and administered, for example, orally, nasally, or by aerosol spray, whereby droplets enter via the mucus membranes of the birds.

Compositions and vaccines of the present invention may include, for example, water or culture medium. Such compositions and vaccines may include one or more suitable pharmaceutically acceptable carriers, stabilizers, preservatives, diluents, and/or buffers. Suitable stabilizers include, for example, SPGA, carbohydrates (such as sorbitol, mannitol, starch, sucrose, dextrin, or glucose), or proteins (such as albumin or casein). A stabilizer is particularly advantageous when a dry vaccine preparation is prepared by lyophilization. Suitable preservatives include, for example, thimerosal, merthiolate, and gentamicin. Diluents include, but are not limited to, water, aqueous buffer (such as buffered saline), alcohols, and polyols (such as glycerol).

A composition or vaccine of the present invention may also include one or more compounds with adjuvant activity. Suitable compounds or compositions for this purpose include aluminum hydroxide, aluminum phosphate, aluminum oxide, plant oils, animal oils, oil-in-water or water-in-oil emulsion based on, for example a mineral oil, such as Bayol F™ or Marcol 52™, Complete Freund's adjuvant, incomplete Freund's adjuvant, or a vegetable oil such as vitamin E acetate, and saponins.

A composition or vaccine of the present invention may further include one or more immunogens derived from other pathogens infectious to poultry. Such immunogens may be derived from, for example, Marek's disease virus (MDV), other serotypes of infectious bronchitis virus (IBV), including, but not limited to, any of those described herein, Newcastle disease virus (NDV), egg drop syndrome (EDS) virus, turkey rhinotracheitis virus (TRTV), poxvirus, reovirus, chicken parvovirus, and avian nephritis virus (including, but not limited to ANV-1 and ANV-2).

Compositions and vaccines of the present invention may be substantially pure. As used herein, "substantially pure" will mean material essentially free of macromolecules or other biological entities that would normally be found with it in nature.

Vaccination for IBV is common for most commercial chickens. The vaccines may be modified-live virus vaccines delivered through mass aerosol applications. The serotypes used in vaccination are often selected based on what serotypes the birds may be exposed to in the field. There is very little cross-protection between different serotypes of IBV. Accordingly, the present invention provides immunological materials that when administered do not result in significant clinical signs or lesions indicative of IBV disease. The present invention also provides immunological materials of low virulence, immunological materials with no increase in virulence when back passaged, and/or immunological materials that prevent infection with virulent wild type strains of IBV.

A composition or vaccine of the present invention may be administered by any suitable known method of inoculating poultry including nasally, ocularly, by injection, in drinking water, in the feed, by exposure, in ovo, maternally, by respiratory inhalation, and the like. The immunogenic composition or vaccine may be administered by mass administration techniques such as by placing the vaccine in drinking water or by spraying or aerosolizing. When administered by injection, the immunogenic composition or vaccine may be administered parenterally. Parenteral administration includes, for example, administration by intravenous, subcutaneous, intramuscular, or intraperitoneal injection.

Compositions and vaccines of the present invention may be administered to birds of any of a variety of avian species that are susceptible to infection with IBV, including, but not limited to, poultry, birds of the order Galliformes, and exotic bird species. Birds of the order Galliformes include, but are not limited to, chickens, turkeys, grouse, quails, and pheasants. As used herein, poultry includes domesticated birds that are kept for the purpose of collecting their eggs or killing for their meat and/or feathers. These most typically are members of the superorder Galloanserae (fowl), especially the order Galliformes (which includes, for example, chickens, quail, turkeys, and grouse) and the family Anatidae (in order Anseriformes), commonly known as "waterfowl" (including, for example, ducks, geese, and swans). Poultry may also include other birds which are killed for their meat, such as pigeons or doves or birds considered to be game, like pheasants. Chickens include, but are not limited to, hens, roosters, broilers, roasters, layers, breeders, the offspring of breeder hens, and layers. As used herein, the term "susceptible to" means the possibility or actuality of a detrimental response to the referenced microorganism, when compared to a non-susceptible individuals or groups, and/or one or more pathological state(s) indicative of avian IBV infection.

The vaccine of the present invention may be administered to poultry before or after hatching. Poultry may receive a vaccine at a variety of ages. For example, broilers may be vaccinated in ovo, at one-day-old, or at 2-3 weeks of age. Laying stock or reproduction stock may be vaccinated, for example, at about 6-12 weeks of age and boosted at about 16-20 weeks of age. Such laying stock or reproduction stock may be vaccinated at about 6, at about 7, at about 8, at about 9, at about 10, at about 11, or at about 12 weeks of age. Also, in some embodiments, such laying stock or reproduction stock may be vaccinated within about the first two weeks of age. Such laying stock or reproduction stock may be boosted at about 16, at about 17, at about 18, at about 19, or at about 20 weeks of age. The offspring of such laying stock or reproduction stock may demonstrate an antibody titer to a polypeptide as described herein, which may prevent or mitigate the symptoms of an IBV infection in the offspring. In ovo vaccination may take place, for example, at about 13 days, about 14 days, about 15 days, about 16 days, about 17 days, about 18 days, about 19 days, about 20 days, or at any range thereof.

Chickens may be vaccinated at any suitable age and are usually about one to three days old before first vaccination. The chickens may be vaccinated only once. Or, if two doses of vaccine are used, the first is given, for example, when the chickens are 3 days to a week old and subsequently after a further 1-10 weeks.

Multiple doses of the composition can be administered throughout the life of the chicken. As maternal immunity is a primary source of providing protection to broiler progeny, breeder chickens are typically vaccinated, although broiler chickens can be vaccinated if so desired.

In some embodiments, a live attenuated IBV isolate of the present invention may be administered at a dose of about $10^{1.5}$ to about $10^{10}$ EID$_{50}$ per bird. In some aspects, a live attenuated IBV isolate of the present invention may be administered at a dose of about $10^{1.5}$ EID$_{50}$ per bird, about $10^{2}$ EID$_{50}$ per bird, about $10^{2.5}$ EID$_{50}$ per bird about $10^{3}$ EID$_{50}$ per bird, about $10^{3.5}$ EID$_{50}$ per bird, about $10^{4}$ EID$_{50}$ per bird, about $10^{4.5}$ EID$_{50}$ per bird, about $10^{5}$ EID$_{50}$ per bird, about $10^{5.5}$ EID$_{50}$ per bird, about $10^{6}$ EID$_{50}$ per bird, about $10^{6.5}$ EID$_{50}$ per bird, about $10^{7}$ EID$_{50}$ per bird, about $10^{7.5}$ EID$_{50}$ per bird, about $10^{8}$ EID$_{50}$ per bird, about $10^{8.5}$ EID$_{50}$ per bird, about $10^{9}$ EID$_{50}$ per bird, about $10^{9.5}$ EID$_{50}$ per bird, about $10^{10}$ EID$_{50}$ per bird, or any range thereof. For example, in some applications, a dose of about $10^{2}$ to about $10^{5}$ EID$_{50}$ per bird may be administered.

A virus, composition, or vaccine as described herein may be administered to poultry or other animals to elicit an immune response to the IBV virus and/or an IBV S1 polypeptide, including, but not limited to the IBV DMV 1639 serotype. An immune response may, for example, include one or more of a cell mediated immune response, which involves the production of lymphocytes in response to exposure to the antigen and/or a humoral immune response, which involves production of plasma lymphocytes (B cells) in response to antigen exposure with subsequent antibody production. A humoral immune response may include an IgG, IgM, IgA, IgD, and/or IgE response. The determination of a humoral or cellular immune response may be determined by any of a variety of methods, including, but not limited to, any of those described herein. The immune response may, or may not, confer protective immunity. Such an immune response may result in a reduction or mitigation of the symptoms of future IBV infection, for example, symptoms of an infection by an IBV virus of the DMV/1639 serotype. Such an immune response may prevent a future IBV infection in poultry, for example, preventing infection by an IBV virus of the DMV/1639 serotype. Immunity may include the induction of a higher level of protection in a population of birds after vaccination compared to an unvaccinated group.

The present invention includes a method of producing an anti-IBV immune response in poultry, the method including administering an isolated virus, composition or vaccine as described herein. In some aspects, immunity includes humoral and/or cellular immunity. In some aspects, immunity includes mucosal immunity.

Administration of an isolated virus, composition, or vaccine as described herein may result in the reduction, inhibition, or prevention of one or more of the disease manifestations of infection with IBV, including one or more of the disease manifestations of infectious bronchitis (IB). Such symptoms may include one or more of body weight suppression, decrease in egg production, mortality, clinical signs (such as, for example, watery eyes, wheezing, snicking, sinus exudate, conjunctivitis, and/or rales), histopathological indications (such as, for example, tracheal lesions), anti-IBV serum antibody titer (determined, for example, by ELISA), and/or IBV viral isolation (measured, for example, by real-time-RT-PCT of tracheal swab samples).

The present invention includes a method of reducing, inhibiting, or preventing an IBV infection in poultry, the method including administering an isolated virus, composition or vaccine as described herein. In some aspects, administration of an isolated virus, composition, or vaccine as described herein reduces, inhibits, or prevents infection with the IBV DMV/1639 variant strain. In some aspects, administration of an isolated virus, composition, or vaccine as described herein provides cross protection, reducing, inhibiting, or preventing one or more of the disease manifestations of infection with a strain of IBV other than the DMV/1639 strain of IBV.

In some aspects of the methods of the present invention, administration includes injection, spraying, oral administration, or respiratory administration. In some aspects of the methods of the present invention, administration induces mucosal immunity. In some aspects of the methods of the present invention, administration includes in ovo administration. In some aspects, in ovo administration includes administration at about 13 days, about 14 days, about 15 days, about 16 days, about 17 days, about 18 days, about 19 days, about 20 days, or any range thereof.

Compositions of matter of the present invention may be substantially pure. As used herein, "substantially pure" will mean material essentially free of any similar macromolecules or other biological entities that would normally be found with it in nature. In some embodiments, the organisms used in such formulations are live. In some embodiments, the organisms, compositions, or vaccines may be lyophilized. The present invention includes isolated viruses. As used herein, "isolated" refers to material removed from its original environment (e.g., the natural environment if it is naturally occurring), and thus is altered "by the hand of man" from its natural state.

Viruses, compositions, and vaccines of the present invention may be administered to birds of any of a variety of avian species that are susceptible to IBV infection, including, but not limited to, poultry, birds of the order Galliformes, and exotic bird species. Birds of the order Galliformes include, but are not limited to, chickens, turkeys, grouse, quails, and pheasants. As used herein, poultry includes domesticated birds that are kept for the purpose of collecting their eggs or killing for their meat and/or feathers. These most typically are members of the superorder Galloanserae (fowl), especially the order Galliformes (which includes, for example, chickens, quail, turkeys, and grouse) and the family Anatidae (in order Anseriformes), commonly known as "waterfowl" (including, for example, ducks, geese, and swans). Poultry may also include other birds which are killed for their meat, such as pigeons or doves or birds considered to be game, like pheasants.

"Poultry" is intended to embrace any breed of chicken, pheasant, emu, ostrich, and other type of bird that is susceptible to infection by IBV. Chickens include, but are not limited to, hens, roosters, broilers, roasters, layers, breeders, the offspring of breeder hens, and layers. In some embodiments, the compositions of matter and methods of the present invention also apply to animals other than poultry that are susceptible to infection with IBV. As used herein, the term "susceptible to" means the possibility or actuality of a detrimental response to the referenced microorganism, such as, for example, reduced vigor or a failure to thrive, when compared to a non-susceptible individuals or groups, and/or one or more pathological state(s) indicative of an IBV infection, including, but not limited to, any of those described herein.

Compositions and vaccines of the present invention may be formulated for delivery by any of a variety of routes known in the veterinary arts, such as for example, mucosal, intranasal, intraocular, or oral administration. Compositions and vaccines of the present invention may be formulated for delivery to the respiratory mucosa and may be administered such that it is immediately or eventually brought into contact with the bird's respiratory mucosal membranes. Compositions and vaccines of the present invention may be formulated for delivery by any of a variety of modes known in the veterinary arts, such as for example, spraying or aerosolizing.

An immunogenic composition or vaccine of the present invention may be administered by any suitable known method of inoculating birds including, but not limited to, nasally, ophthalmically, by eye drop, by injection, in drinking water, in the feed, by exposure, in ovo, maternally, and the like.

The immunogenic composition or vaccine may be administered by mass administration techniques such as by placing the vaccine in drinking water or by spraying the animals' environment. A composition may be administered by spraying an individual or the flock with a solution, such aerosol delivery may involve the administration of the composition incorporated in small liquid particles. Such spray-type particles may have a droplet size ranging from between about 10 to about 100 microns, more preferably, a droplet size from between about <1 to about 50 microns. For the generation of the small particles, conventional spray-apparatus and aerosol generators may be used, such as the commercially available spray generators for knapsack spray, hatchery spray and atomist spray. Administration through drinking water may be carried out using conventional apparatus. When administered by injection, the immunogenic composition or vaccine may be administered parenterally. Parenteral administration includes, for example, administration by intravenous, subcutaneous, intramuscular, or intraperitoneal injection.

A composition or vaccine of the present invention may be administered to birds before or after hatching. Birds may receive such a composition of vaccine at any of a variety of ages. With delivery after hatching, materials may be delivered, for example, about one week after hatching, about two weeks after hatching, about three weeks after hatching, about four weeks after hatching, about five weeks after hatching, about six weeks after hatching, or any range thereof. For in ovo administration, materials may be delivered about seventeen days of incubation, about eighteen days of incubation, about nineteen days of incubation, about twenty days of incubation, and any range thereof.

The viruses of the present invention may be utilized in any of the commonly used methods for IBV detection, such as, for example, hemagglutination (HA) (Lashgari et al. *Avian Dis* 28, 435-443 (1984)), hemagglutination inhibition (King et al. *Avian Dis* 27, 100-112 (1983)), AGPT (Lohr *Avian Dis* 24, 463-467 (1980); *Lohr Avian Dis* 25, 1058-1064 (1981)), RT-PCR (Kwon et al. *Avian Dis* 37, 194-202 (1993)), and real-time RT-PCR (Callison et al. *J Virol Methods* 138, 60-65 (2006)).

Exemplary Embodiments of the present invention include, but are not limited to, the following.

1. An infectious bronchitis virus (IBV) isolate, wherein the IBV isolate comprises the heat attenuated IBV isolate PDRC DMV/1639 deposited at the ATCC under Patent Designation PTA-126757 or a progeny or derivative thereof, wherein a progeny or derivative thereof has essentially the same biological and serological characteristics of the heat attenuated IBV isolate PDRC DMV/1639 deposited at the ATCC under Patent Designation PTA-126757.
2. The IBV isolate of Embodiment 1, wherein the IBV isolate is lyophilized, freeze dried, or frozen.
3. A composition comprising the IBV isolate of Embodiments 1 or 2.
4. The composition of Embodiment 3 further comprising a pharmaceutically acceptable carrier.
5. A vaccine comprising the isolated IBV isolate or a progeny or derivative thereof of Embodiments 1 or 2 or a composition of Embodiments 3 or 4.
6. The vaccine of Embodiment 5, wherein the vaccine reduces one or more of the clinical signs and/or the viral load induced by an IBV infection in poultry.
7. A vaccine for birds of the order Galliformes comprising an amount of the heat attenuated IBV isolate PDRC DMV/1639 deposited at the ATCC under Patent Designation PTA-126757, or a progeny or derivative thereof, sufficient to protect the birds from one or more clinical signs induced by an infectious bronchitis virus (IBV) infection in poultry.
8. The composition or the vaccine of any one of Embodiments 3 to 7, further comprising an adjuvant.
9. The composition or vaccine of any one of Embodiments 3 to 8, further comprising other viral material.
10. The composition or vaccine of any one of Embodiments 3 to 9, wherein the composition or formulation is formulated for intranasal, intraocular, oral, mucosal, intramuscular, subcutaneous, or in ovo administration.
11. The composition or vaccine of any one of Embodiments 3 to 10, wherein the composition or vaccine is formulated for spraying or aerosolizing.
12. An effervescent tablet comprising an IBV isolate or a progeny or derivative thereof, composition, or vaccine of any one of Embodiments 1 to 11.
13. A method of producing an immune response to an infectious bronchitis virus (IBV) in poultry, the method comprising administering the IBV isolate or a progeny or derivative thereof, composition, vaccine, or effervescent table of any one of Embodiments 1 to 12 to the poultry.
14. A method of producing anti-IBV antibodies in poultry, the method comprising administering the IBV isolate or a progeny or derivative thereof, composition, vaccine, or effervescent tablet of any one of Embodiments 1 to 12 to the poultry.
15. A method of reducing one or more clinical signs and/or viral load induced by an infectious bronchitis virus (IBV) infection in poultry, the method comprising administering an effective amount of the IBV isolate or a progeny or derivative thereof, composition, vaccine, or effervescent tablet of any one of Embodiments 1 to 12 to the poultry.
16. A method for reducing susceptibility of a bird of the order Galliformes against infectious bronchitis virus (IBV) infection, the method comprising administering to the bird an effective amount of the IBV isolate or a progeny or derivative thereof, composition, vaccine, or effervescent tablet of any one of Embodiments 1 to 11.

17. A method for protecting a bird of the order Galliformes against infectious bronchitis virus (IBV) infection, the method comprising administering to the bird an effective amount of the IBV isolate or a progeny or derivative, composition, vaccine, or effervescent tablet of any one of Embodiments 1 to 11.

18. The method of any one of Embodiments 13 to 17, wherein administration is intranasal, intraocular, oral, mucosal, intramuscular, or subcutaneous.

19. The method of any one of Embodiments 13 to 18, wherein administration comprises in ovo administration.

20. The method of any one of Embodiments 13 to 19, wherein the IBV isolate or a progeny or derivative thereof, composition, or vaccine is administered by aerosol.

21. The method of any one of Embodiments 13 to 19, wherein the IBV isolate or a progeny or derivative, composition, or vaccine is administered by spraying.

22. The method of any one of Embodiments 13 to 19, wherein the IBV isolate or a progeny or derivative, composition, or vaccine is administered by drinking water.

23. The method of any one of Embodiments 13 to 22, wherein administration comprises administration to a breeder hen.

24. The method of any one of Embodiments 13 to 23, wherein the poultry comprises a bird of the order Galliformes.

25. The method of any one of Embodiments 13 to 24, wherein the bird is a chicken or turkey.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

In several places throughout the application, guidance is provided through lists of examples, which examples can be used in various combinations. In each instance, the recited list serves only as a representative group and should not be interpreted as an exclusive list. It is to be understood that the particular examples, materials, amounts, and procedures are to be interpreted broadly in accordance with the scope and spirit of the invention as set forth herein.

All headings throughout are for the convenience of the reader and should not be used to limit the meaning of the text that follows the heading, unless so specified.

The present invention is illustrated by the following examples. It is to be understood that the particular examples, materials, amounts, and procedures are to be interpreted broadly in accordance with the scope and spirit of the invention as set forth herein.

EXAMPLES

Example 1

Live, Heat Attenuated IBV Strain DMV1639 for Use as a Vaccine in Poultry

Heat treatment was used to attenuate the DMV/1639 strain of avian coronavirus infectious bronchitis virus. Briefly, the original sample was taken in 2019 from a broiler farm in Georgia experiencing respiratory signs. The virus was isolated and then passaged 3 times in embryonated eggs. This sample (total pass 4) was then heat shock attenuated through 14 heat shock passages, following the previously published method of attenuation of Jackwood, et al. (Jackwood et al. *Avian Pathol* 39, 227-233 (2010)). The virus recovered after heat shock passage 14 (hsp14) was then passaged through embryonated eggs once to expand the virus, resulting in a total of 19 passages, 5 traditional passages and 14 heat shock passages.

As described in the following examples, the treated virus was propagated in embryonated eggs and tested for safety and efficacy in poultry. Using the criteria of Title 9 of the Code of Federal Regulations (CFR) for IBV vaccine testing, the attenuated virus passed both the safety test and the efficacy test. This strain of DMV/1639 is a recent virus isolated from Georgia and represents the evolved version of this virus causing upper-respiratory tract disease in poultry. It is currently a significant economic problem in the poultry industry and continues to spread. Currently there is no commercial vaccine for this strain of IBV.

This live, heat attenuated isolate of the IBV strain DMV/1639 (also referred to herein as heat attenuated DMV/1639, attenuated DMV/1639, PDRC DMV/1639, heat attenuated PDRC DMV/1639, heat attenuated PDRC DMV/1639 and Attenuated DMV/1639—Georgia Isolate) was deposited with the American Type Culture Collection (ATCC®) Patent Depository, 10801 University Boulevard, Manassas, Virginia 20110 USA on May 15, 2020, as Patent Deposit Number PTA-126757.

Example 2

Comparison of Heat Attenuated PDRC DMV1639, DE1639, Ma5, and iBron GA08 for Homologous and Heterologous Protection Ability The concept of cross protection for IBV vaccines has been studied extensively when combining multiple IBV vaccine types together, usually Ma5 and 4/91. Recently, some vaccine manufacturers have suggested that a single IBV vaccine may be able to cross protect against heterologous challenge serotypes, without the need for additional IBV vaccines. Additionally, it seems that some vaccines in use may not be completely protective against current homologous viruses circulating in the field. To investigate these questions, four different vaccines were tested against a pathogenic DMV/1639 challenge to evaluate protection.

Materials and Methods

Viruses. The Mass type (Boehringer Ingelheim), iBron GA08 type (Ceva), DE1639 (also referred to herein as autogenous DMV/1639 and MA DMV/1639), and an attenuated (by heat treatment) PDRC DMV/1639 vaccine were used in this study. The challenge virus used is a recent isolate of DMV/1639/11.

Experimental Design. The experimental design is shown in Table 1. One-day old maternal antibody positive broiler chicks were used for this experiment. One hundred chicks for each group were vaccinated by spray with a full dose of each vaccine at 1-day of age and placed, by group, into colony houses. On day 7, all chicks in each group were swabbed and vaccine virus was detected using real time RT-PCR. At 28 days of age, 10 birds for each challenge virus and 5 birds for each control group were moved into isolators and challenged with $1 \times 10^4$ $EID_{50}$ of DMV/1639/11. The titer of the challenge virus was verified by back titration in embryonated eggs. Necropsy was performed 5 days post challenge. The DE1639 vaccine group was held in the colony house and swabbed until 42 days of age for vaccine rolling evaluation.

TABLE 1

Experimental design.

| Challenge Vaccine | Vaccinated | Challenged with DMV/1639/11 | None |
|---|---|---|---|
| DE1639 | 100 | 10 | 5 |
| DE1639 + Mass | 100 | 10 | 5 |
| iBron | 100 | 10 | 5 |
| DE1639 + iBron | 100 | 10 | 5 |
| Mass + iBron | 100 | 10 | 5 |
| PDRC DMV/1639 | 100 | 10 | 5 |
| None | 5 | 5 | 5 |

Necropsy/Clinical Signs. Clinical signs were recorded and scored based on published laboratory scoring methods (Jackwood et al. *Avian Dis* 59, 368-374 (2015)) where a 0=no signs, 1=slight wheezing or snicking, 2=more pronounced wheezing, sinus exudate, conjunctivitis, and 3=rales.

Necropsy/RNA extraction and challenge virus detection by real time RT-PCR. At necropsy, intrachoanal swabs from the oropharyngeal area in the palatine cleft were collected and placed into 1 ml of ice cold PBS for virus detection by real time RT-PCR. Viral RNA was extracted from 50 ul of the PBS using the MagMAX-96 RNA Isolation Kit (Ambion Inc., Austin Tex.) according to the manufacturer's protocol on a KingFisher magnetic particle processor (Thermo Scientific, Waltham, MA). Real time RT-PCR was conducted using an Applied Biosystems 7500 Fast Real-Time PCR System (Life Technologies, Carlsbad, CA) and the AgPath-ID™ One-Step RT-PCR kit (Ambion Inc.) according to the manufacturer's recommendations. Primers and probe for the real time RT-PCR correspond to the specific serotype being tested. The primers were obtained from Integrated DNA Technologies (Coralville, IA) and Taqman probe was synthesized by BioSearch Technologies (Novato, CA).

Results

Figure 1B:
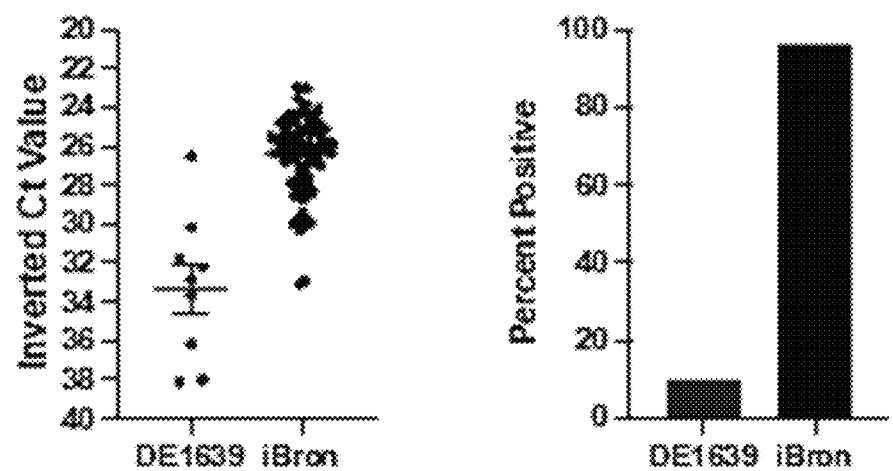
Figure 1B:
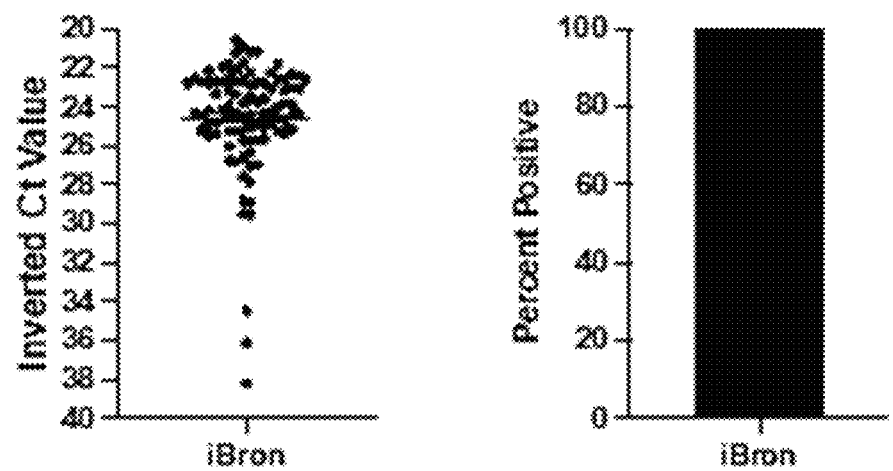
Figure 1B:
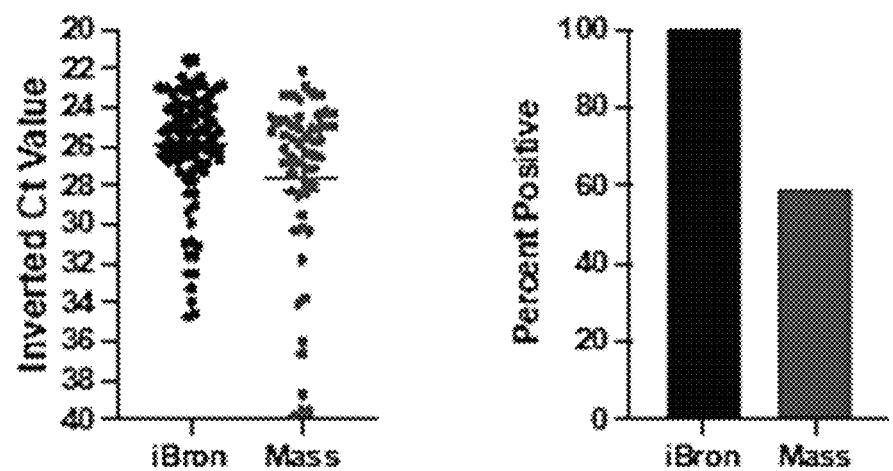

For this trial, 100 chicks were spray vaccinated with the vaccines indicated in Table 1. All 100 chicks in each group were then placed into colony type houses on fresh litter to mimic environmental conditions in the field. At 7 days post vaccination (dpv), all chicks in each group were swabbed in the choanal cleft to measure vaccine virus present, and the data can be seen in FIGS. 1A and 1B. As expected, based on previous vaccine take sampling, the DE1639 vaccine only infected ~60% of the chicks during vaccination, and the resulting viral load was relatively low (~33 mean Ct value). This is contrasted by the PDRC DMV/1639 vaccine developed at the PDRC that infected nearly 100% with a mean Ct value of ~26.5. When combining the DE1639 vaccine with other vaccines, the infection rate actually dropped compared to using the single vaccine. When combined with the Mass vaccine, the DE1639 vaccine only infected ~35% of the chicks, while the viral load was the same (~32 Ct value).

The Mass vaccine infected at 100% with a mean Ct value of ~25, demonstrating that it was not a vaccine application issue that caused the vaccination failure for the DE1639 vaccine for this group. The same trend is seen when the DE1639 vaccine is combined with iBron from Ceva, where only ~10% of the chicks were positive with a ~33 Ct value for the autogenous DMV/1639. Chicks were ~95% positive for iBron with a mean Ct value ~26, again demonstrating that it was not an application issue. When evaluating iBron by itself, nearly 100% of the chicks were positive with a mean Ct of ~25, indicating good take and replication. Interestingly, when looking at iBron mixed with the Mass vaccine, chicks were still 100% positive for iBron with a mean Ct of ~26, but only 60% of the chicks were positive for Mass with a mean Ct of ~27.5. However, there is a "tail" of positive values that indicated not all the birds were vaccinated evenly with Mass. It seems that there may be some vaccine interference when combining iBron (a strong vaccine) with the DE1639 or Mass from BI (weaker vaccines).

Figure 2:
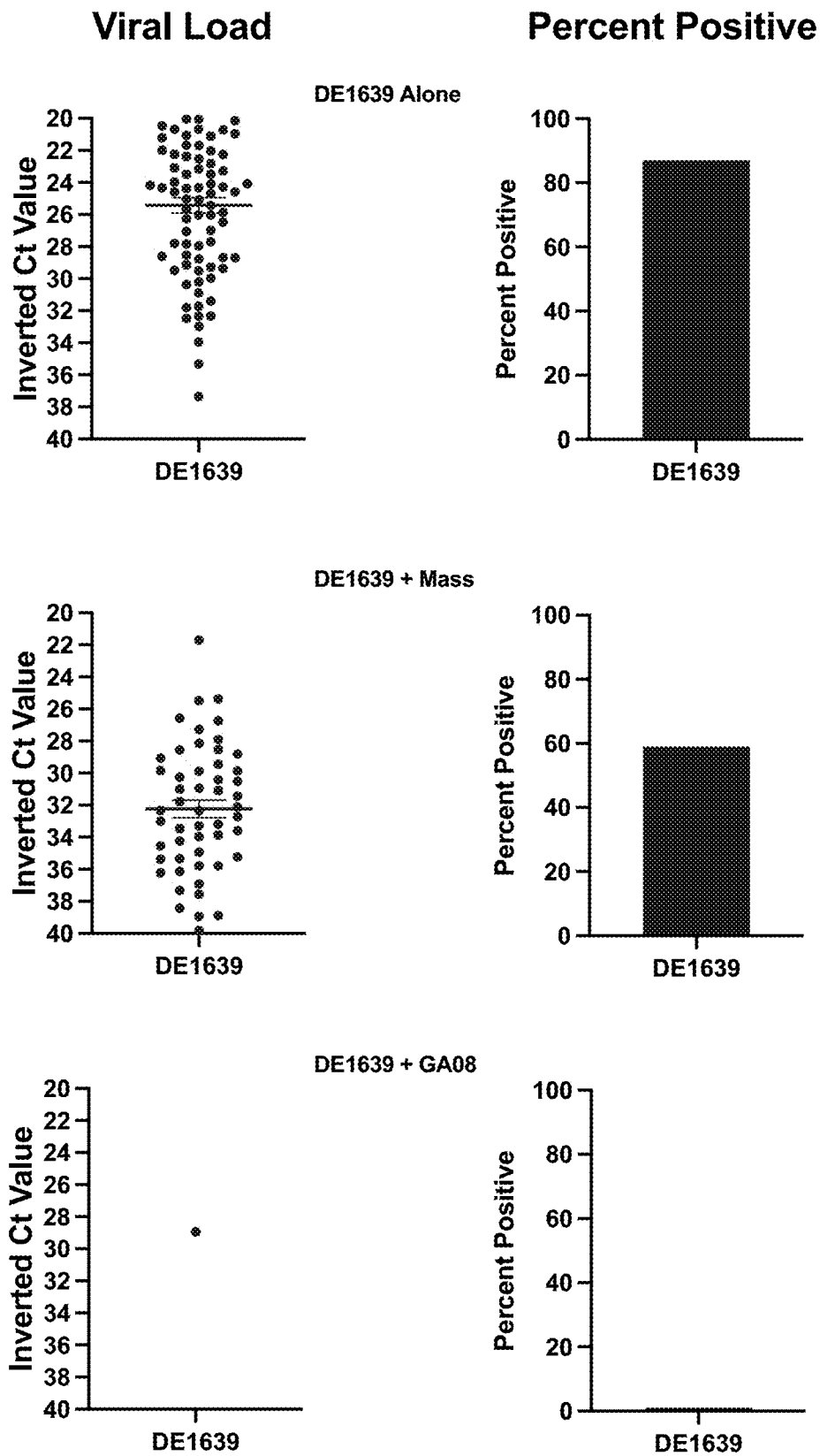
FIG. 2. Day 14 takes for the autogenous DE1639 vaccinated chickens.
Figure 3A:
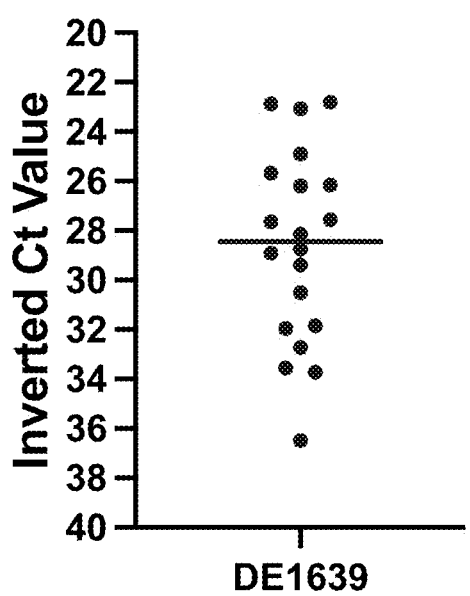
FIGS. 3A and 3B. Day 28 viral loads for the autogenous DE1639 only vaccinated chickens.
Figure 3B:
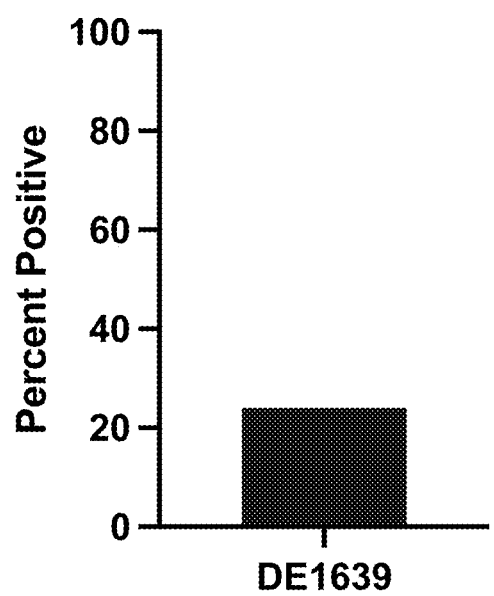

Since 7 day takes were not good for the DE1639 vaccinated groups, it was decided to swab those groups receiving that vaccine again at day 14 to evaluate viral load and potential vaccine rolling. This data can be seen in FIG. 2. Both percent positive (~85%) and viral load (mean Ct of 25.5) increased in the DE1639 only vaccinated group at day 14 compared to day 7. This would indicate that the peak of viral vaccine replication is occurring much later for this vaccine than traditional IBV vaccines. The percent positive for the DE1639 vaccine in the group vaccinated with this vaccine and Mass increased as well (from ~35% positive at day 7 to ~60% positive at day 14), but the mean viral load (Ct of ~32) did not change. This would indicate that there is still vaccine suppression occurring between the Mass vaccine and the DE1639 vaccine, and the conditions for a rolling reaction, with portions of the population becoming positive at different times, are being established. For the DE1639 and iBron vaccinated group, only one sample was positive, indicating that the iBron vaccine is essentially shutting down the DE1639 vaccine. The DE1639 vaccine only group was also swabbed at 28 dpv to see how much vaccine was still present. Results are shown in FIGS. 3A and 3B. Approximately 25% of the birds were still positive, with viral loads ranging from Ct values of 36 to 22 (mean Ct ~28). This shows that vaccine is continuing to roll in the flock.

One other notable observation was that the groups that were given iBron vaccine alone or in combination with another vaccine exhibited significant clinical respiratory signs at 7 and 14 days post vaccination. Rales were observed in ¼-⅓ of the chicks when swabbing to measure vaccine takes. No clinical respiratory signs were noticed in any other vaccine groups.

Figure 4:
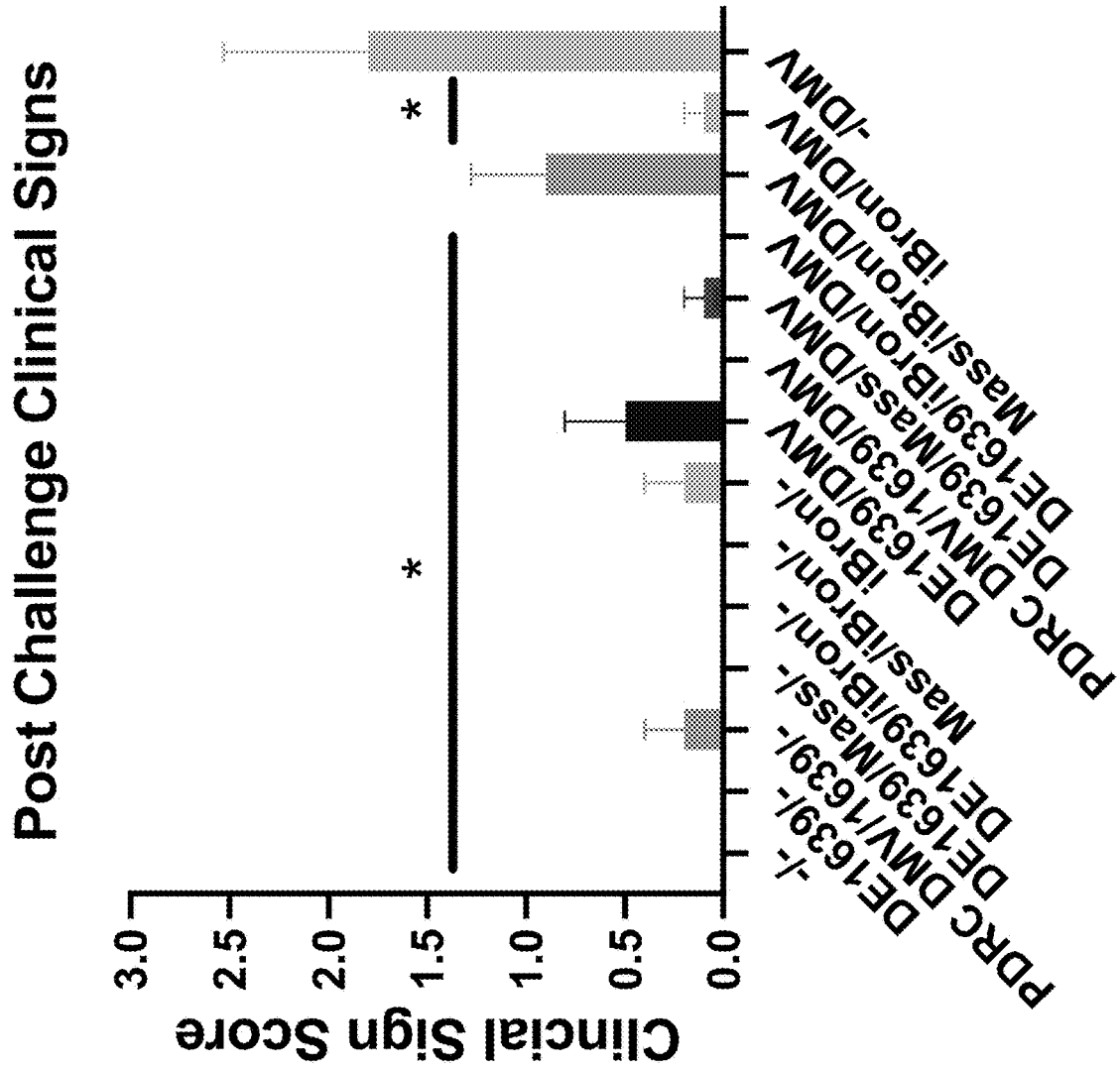
FIG. 4. Post challenge clinical signs by vaccine/challenge group.

Chickens in each vaccine group were challenged at 28 days post vaccination with a pathogenic DMV/1639 type D3 virus at ~1×10$^4$ EID$_{50}$ per bird. Five days post challenge, clinical respiratory signs were recorded, and swabs were taken for IBV load analysis by PCR. All groups had statistically significantly lower clinical signs than the non-vaccinated, DMV/1639 challenged group except the Mass/iBron vaccinated and challenged group, though all groups were numerically scored lower. Results are shown in FIG. 4. This is not surprising based on previous results from vaccine challenge studies using DMV/1639 type challenge viruses and numerous IBV vaccines.

Figure 5:
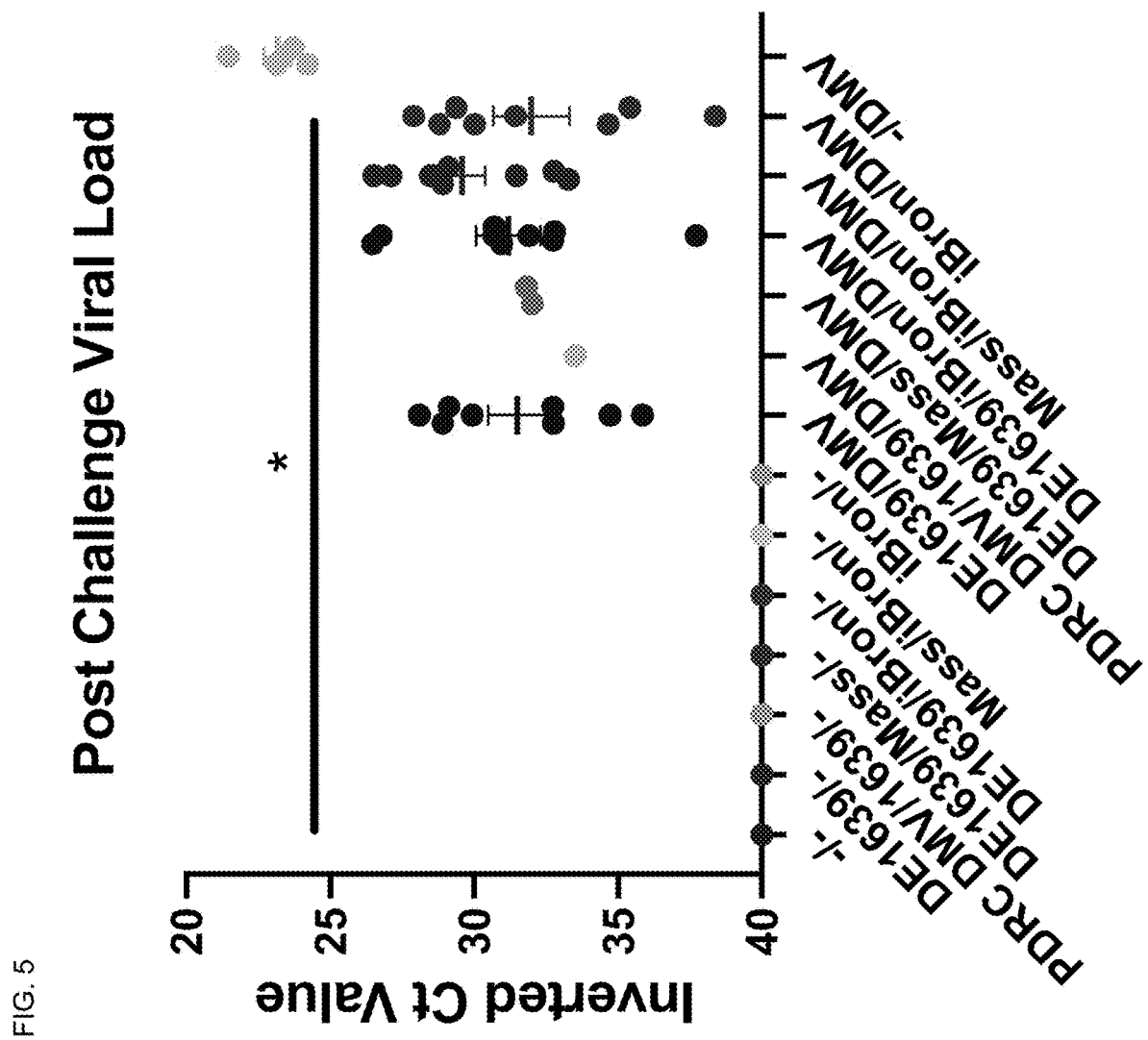
FIG. 5. Viral load post-challenge based on PCR detection of DMV specific virus.

Viral loads as determined by DMV/1639 type specific PCR showed that all groups had statistically significantly lower viral loads than the non-vaccinated, challenged group. Results are shown in FIG. 5. Overall, the mean Ct value of the non-vaccinated, challenged group was ~23, and all 5 samples were very close to this value. The group vaccinated with the DE1639 vaccine had 8/10 samples positive for virus after challenge, but the samples broke into two distinct groups. One group clustered around the 29 Ct value mark and the other group clustered around the 34 Ct value mark.

Since this assay cannot differentiate vaccine from challenge virus, it is impossible to say that all or none of these positive samples are vaccine or challenge. But based on the day 28 samples from this group and experience when performing these studies, one would estimate that half of these positive values are from challenge virus. The PDRC DMV/1639 vaccinated group only had one positive sample post challenge, with a Ct value of ~33, indicating little virus present. This test shows that the PDRC DMV/1639 vaccine was fully protective against this challenge virus based on 9-CFR standards (90% or >samples were negative for virus). The group vaccinated with the DE1639 and Mass vaccines only had 2 samples positive post challenge, with a mean Ct value of ~32. This is interesting considering the DE1639 vaccine seemed to be suppressed to an extent when combined with the Mass vaccine. But it can also not be ruled out that in randomly selecting chickens for challenge, we inadvertently selected chickens that did receive DMV/1639 vaccine and thus did develop some immunity. The group that was vaccinated with the DE1639 vaccine and iBron had 8/10 samples positive with a mean Ct value of ~31. The Ct values in this group ranged from ~26-38, indicating that only partial protection from the challenge was achieved.

It would seem that the suppression of the DE1639 vaccine by the iBron vaccine did affect the development of specific neutralizing antibodies against the DMV/1639 challenge. For the Mass and iBron and iBron only vaccine groups, 9/10 and 8/10 samples were positive post challenge with mean Ct values of ~30 and 32, respectively. These two groups were very similar in mean Ct and total number positive post challenge to the DE1639 and iBron vaccine group, indicating that specific neutralizing antibodies were not properly developed in any of these groups.

Discussion

Based of field observations, the experiment concluded as expected. The DE1639 vaccine did not fully infect at the time of initial vaccination, and then lingered in the birds until at least the challenge timepoint. Furthermore, virus was detected post-challenge at a rate higher than vaccine was detected prior to challenge, indicating that at least some of the virus detected after challenge was challenge virus. This means either the DE1639 vaccine is not a perfect antigenic match to the challenge, or the birds that did not get vaccinated due to the poor infection rate were not protected from the challenge. Either way, this vaccine was not effective at stopping the challenge virus.

The same could be said of the DE1639 and iBron, Mass and iBron, and iBron only vaccinated groups. In those groups, nearly all birds received the iBron vaccine, and subsets of the birds received the other vaccine in the combination. This indicates that the iBron vaccine was suppressing the other vaccines to an extent, and that the iBron vaccine by itself is not fully protective.

The only group that was fully protected (90% or >were negative) was the group vaccinated with the PDRC DMV/1639 vaccine. This was developed from a recent 2019 isolate and it appears to be a good antigenic match to the field virus. Also, this vaccine was given at a lower titer than the other vaccines (~1×10$^{3.5}$ EID$_{50}$), but still had near perfect infection and replication dynamics.

The DE1639 vaccine does not provide good protection from a challenge, and the vaccine persists in the flock setting up a rolling reaction scenario and clouding the diagnostic picture. The combination of Mass and iBron protected as well as the DE1639 vaccine when evaluating virus detection post-challenge, and other experiments have shown similar results for this combination. This vaccine combination can reduce clinical signs and potentially reduce the effects of the challenge on performance and condemnations, but it does not fully stop the DMV/1639 challenge virus from infecting and replicating.

Example 3

Comparison of the Current DE1639 Vaccine and the DMV/1639 Vaccine for Homologous Protection Ability The DMV/1639 IB virus has been continually circulating in poultry flocks since at least 2014, despite the use of a live-attenuated autogenous vaccine in some production companies. It seems that this vaccine in use may not be completely protective against current homologous viruses circulating in the field. For this reason, the novel heat-attenuated DMV/1639 vaccine of the present invention was produced in an effort to increase the protection against currently circulating field viruses of this variant serotype.

Materials and Methods

Viruses. A heat-attenuated live virus DMV/1639 type vaccine developed by the University of Delaware (DE1639) and the attenuated PDRC DMV/1639 vaccine as described herein (deposited at the ATCC under Patent Designation PTA-126757) were used in this study. The challenge virus used was a recent isolate of DMV/1639/11 from a broiler flock on the DelMarVa peninsula.

Experimental Design. The experimental design is shown in Table 2 below. One-day old maternal antibody positive broiler chicks were used for this experiment. One hundred chicks for each group were vaccinated by spray with a full dose of each vaccine at 1-day of age and placed, by group, into colony houses. On day 7, all chicks in each group were swabbed and vaccine virus was detected using real time PCR. At 28 days of age, 10 birds for each challenge virus and 5 birds for each control group were moved into isolators and challenged with $1 \times 10^4$ $EID_{50}$ of DMV/1639/11. The titer of the challenge virus was verified by back titration in embryonated eggs. Necropsy was performed 5 days post challenge.

Necropsy/Clinical Signs. Clinical signs were recorded and scored based on published laboratory scoring methods (Jackwood et al. *Avian Dis* 59, 368-374 (2015)), where a 0=no signs, 1=slight wheezing or snicking, 2=more pronounced wheezing, sinus exudate, conjunctivitis, and 3=rales.

Necropsy/RNA extraction and challenge virus detection by real time RT-PCR. At necropsy, intrachoanal swabs from the oropharyngeal area in the palatine cleft were collected and placed into 1 ml of ice cold PBS for virus detection by real time RT-PCR. Viral RNA was extracted from 50 ul of the PBS using the MagMAX-96 RNA Isolation Kit (Ambion Inc., Austin Tex.) according to the manufacturer's protocol on a KingFisher magnetic particle processor (Thermo Scientific, Waltham, MA). Real time RT-PCR was conducted using an Applied Biosystems 7500 Fast Real-Time PCR System (Life Technologies, Carlsbad, CA) and the AGPATH-ID™ One-Step RT-PCR kit (Ambion Inc.) according to the manufacturer's recommendations. Primers and probe for the real time RT-PCR correspond to the specific serotype being tested for. The primers were obtained from Integrated DNA Technologies (Coralville, IA) and TAQMAN® probe was synthesized by BioSearch Technologies (Novato, CA).

Results

Purity Testing. The PDRC DMV/1639 vaccine was tested for purity by quantitative real-time PCR using primers and probes that will detect all know serotypes of IBV in the United States. Table 3 below shows that the vaccine only tested positive for DMV/1639, showing that no other IBV contaminants were present. The vaccine was also streaked onto a blood agar bacterial plate, and no growth was detected at 24 or 48 hours of incubation.

TABLE 3 qRT-PCR of PDRC DMV/1639 Vaccine.

| | Target | Ct | Target | Ct | Target | Ct | Target | Ct |
|---|---|---|---|---|---|---|---|---|
| PDRC DMV/1639 Vaccine | Generic IBV | 18.0197 | Arkansas | Negative | GA08 | Negative | Mass | Negative |
| | DMV/1639 | 14.9809 | Del072/GA98 | Negative | GA13 | Negative | Conn | Negative |

TABLE 2

Experimental design.

| Challenge Vaccine | Vaccinated | Challenged with DMV/1639/11 | None |
|---|---|---|---|
| DE1639 | 100 | 10 | 5 |
| PDRC DMV/1639 | 100 | 10 | 5 |
| None | 5 | 5 | 5 |

Safety Study. The virus used in the vaccine experiment was used for a safety study following USDA 9CFR guidelines. The titer of the vaccine actually given to chicks in the efficacy study was $1 \times 10^{3.4}$ $EID_{50}$, and at least a 10× dose was needed for the safety study. To that end, a dose of $3.16 \times 10^5$ $EID_{50}$ was administered by the oculonasal route individually to 26 SPF chicks on day of hatch. Four SPF chicks were kept non-vaccinated as a comparative negative control. The 26 vaccinated chicks were separated into two isolators, one with 15 chicks and the other with 11 chicks. All chicks were monitored daily for a total of 21 days for any exaggerated clinical signs associated with IBV vaccine infection or mortality. Two chicks were euthanized during the trial for splayed legs, but did not show any signs of IBV infection and necropsy did not reveal any lesions typical of IBV. No chicks in the study showed any signs of IBV for the 21 day experiment. Results of the daily monitoring can be seen in Table 4 below.

TABLE 4

Safety Study.

| SPE/Birds # | day of age | 10 times challenge dose | Vaccination Day one | Observation 21 days |
|---|---|---|---|---|
| 26 | 1 | $3.1610^5$ $EID_{50}$/ml | Feb. 25, 2020 | Mar. 17, 2020 finish |
| 4 | 1 | No V | | |

| | Cage group | | |
|---|---|---|---|
| date inoculation | 4 407(Control)(Birdnumber) | 15 408 (Sample Group) | 11 409(Sample group) |
| 25-Feb | good (4) | good (15) | good(11) |
| 26-Feb | good (4) | good (15) | good(11) |
| 27-Feb | good (4) | good (15) | good(11) |
| 28-Feb | good (4) | good (15) | good(11) |

TABLE 4-continued

Safety Study.

| 29-Feb | good (4) | good (15) | good(11) |
|---|---|---|---|
| 1-Mar | good (4) | 1 euthanized/splayed leg | 1 euthanized/splayed leg |
| 2-Mar | good (4) | good (14) | good(10) |
| 3-Mar | good (4) | good (14) | good(10) |
| 4-Mar | good (4) | good (14) | good(10) |
| 5-Mar | good (4) | good (14) | good(10) |
| 6-Mar | good (4) | good (14) | good(10) |
| 7-Mar | good (4) | good (14) | good(10) |
| 8-Mar | good (4) | good (14) | good(10) |
| 9-Mar | good (4) | good (14) | good(10) |
| 10-Mar | good (4) | good (14) | good(10) |
| 11-Mar | good (4) | good (14) | good(10) |
| 12-Mar | good (4) | good (14) | good(10) |
| 13-Mar | good (4) | good (14) | good(10) |
| 14-Mar | good (4) | good (14) | good(10) |
| 15-Mar | good (4) | good (14) | good(10) |
| 16-Mar | good (4) | good (14) | good(10) |
| 17-Mar | good (4) | good (14) | good(10) |

Figure 6:
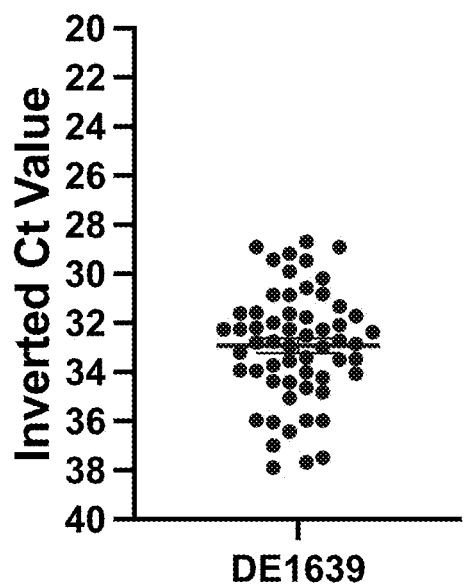
FIG. 6. Day seven vaccine takes for DE1639 and PDRC DMV/1639 vaccinated chicks.
Figure 6:
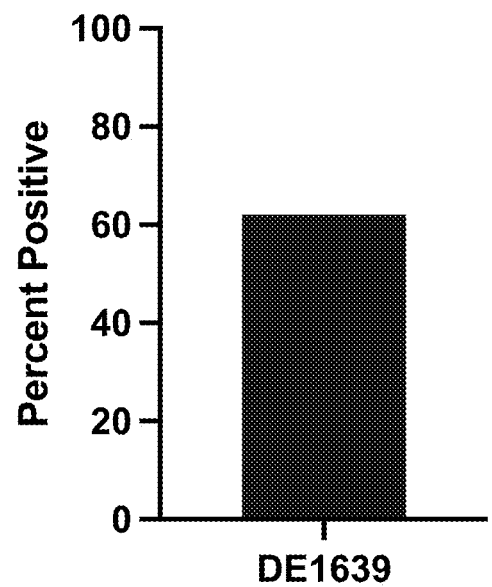
Figure 6:
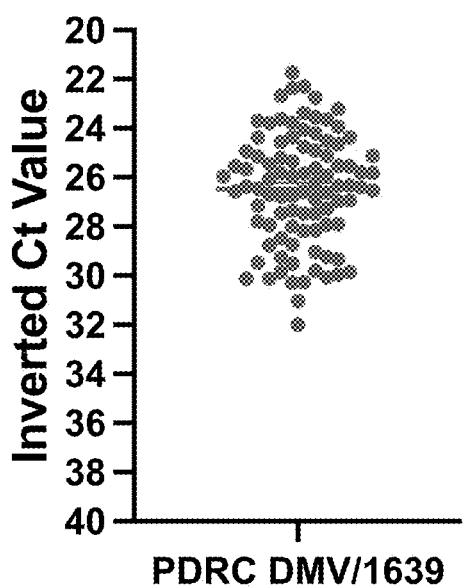
Figure 6:
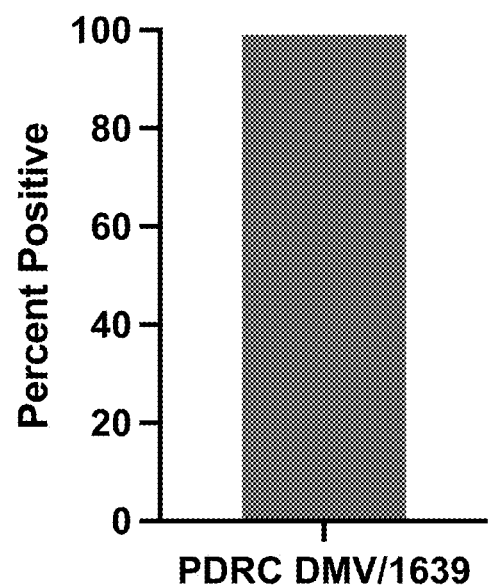
Figure 7:
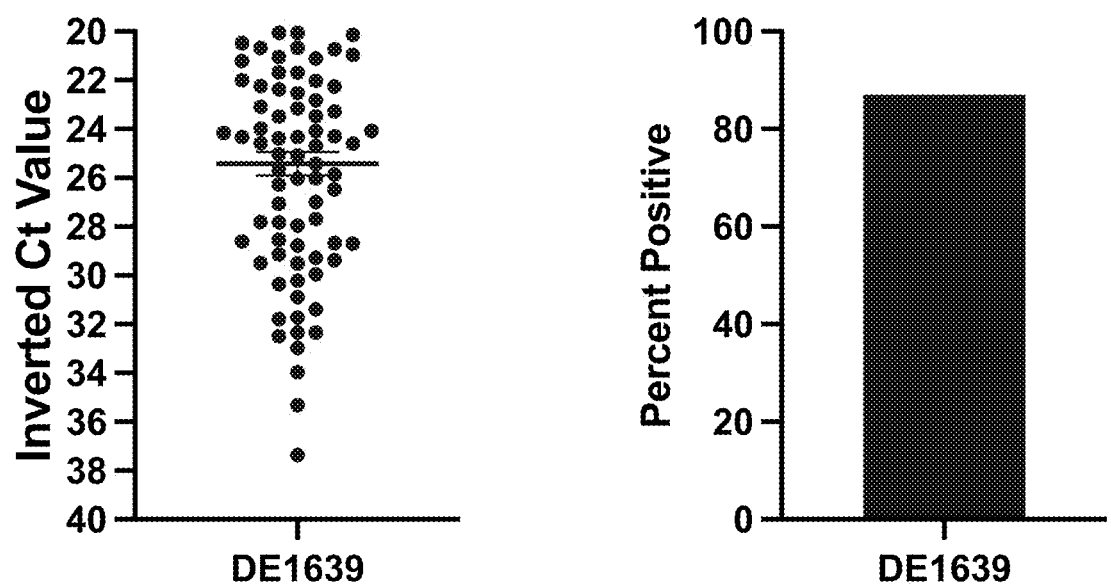
FIG. 7. Day 14 takes for DE1639 vaccinated chickens.
Figure 8:
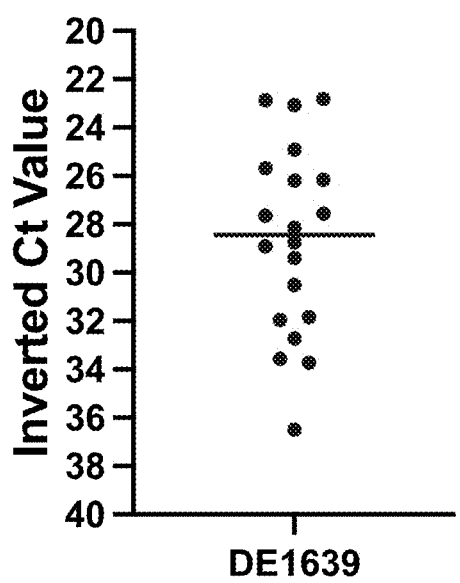
FIG. 8. Day 28 viral loads for DE1639 only vaccinated chickens prior to challenge.
Figure 8:
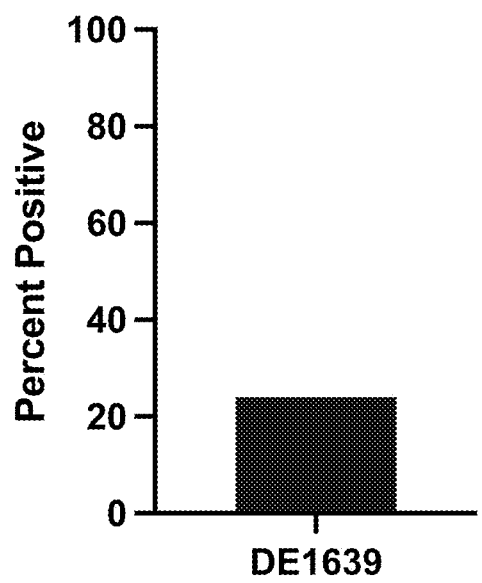
Figure 10:
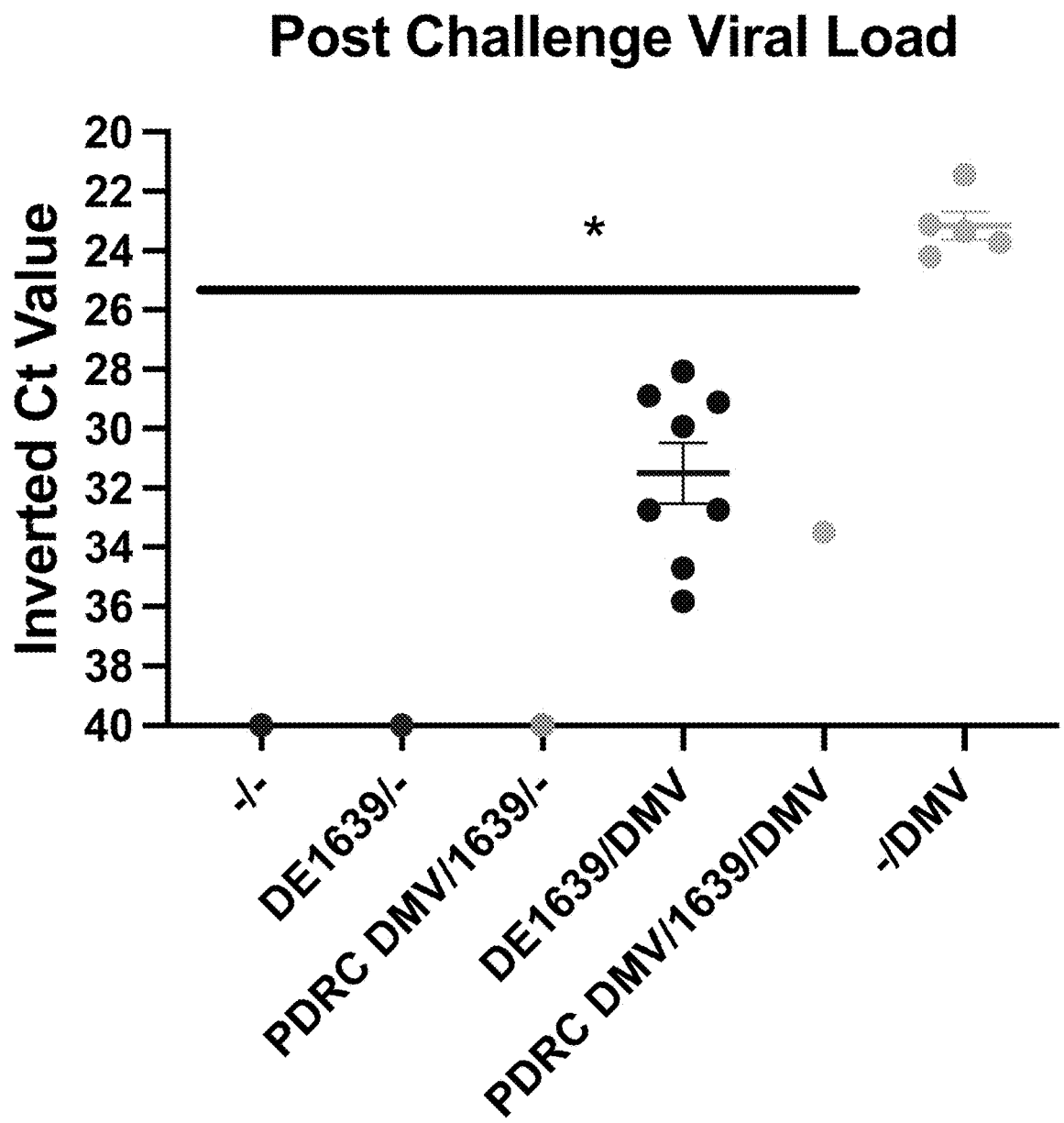
FIG. 10. Viral load post-challenge based on PCR detection of DMV specific virus.
Figure 11:
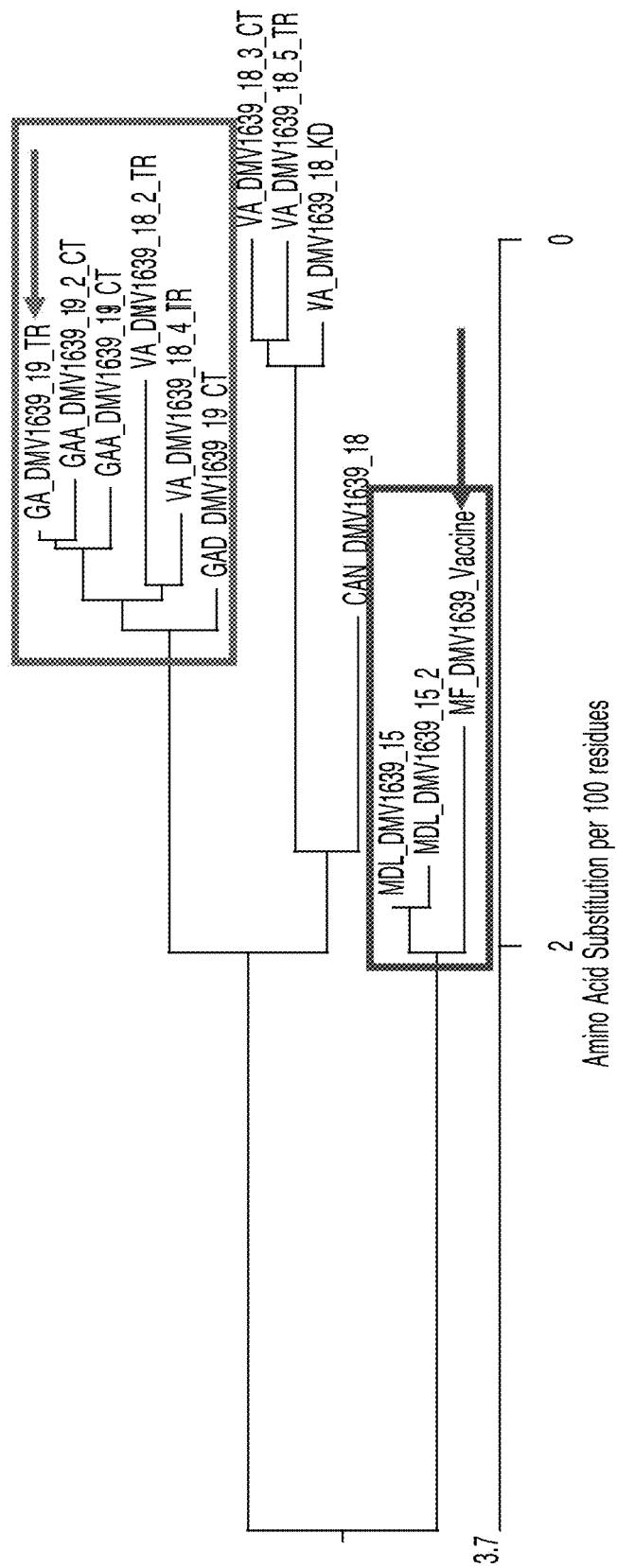
FIG. 11. Phylogenetic Tree comparing the different isolates of the DMV/1639 virus. The lower box represents isolates from the original 2015 outbreak, with the autogenous vaccine indicated with the arrow. The more recent isolates from 2019 are in the upper box, with the PDRC vaccine indicated by the arrow.

Only record clinical sign
Rale (R),
conjectivitis (CJ),
nostril edischarge (ND),
Dull (D)
Good: No clinical signs Efficacy Study. For this trial, 100 chicks at a time were spray vaccinated with the vaccines indicated in Table 2. All 100 chicks in each group were then placed into colony type houses on fresh litter to mimic environmental condition in the field. At 7 days post vaccination (dpv), all chicks in each group were swabbed in the choanal cleft to measure vaccine virus present. All of the data can be seen in FIG. 6. As expected, based on previous vaccine take sampling, the DE1639 vaccine only infected ~60% of the chicks during vaccination, and the resulting viral load was relatively low (~33 mean Ct value). This is contrasted by the DMV/1639 vaccine described herein (PDRC DMV/1639) that infected nearly 100% with a mean Ct value of ~26.5 (FIG. 6).

Since 7 day takes were not good for the DE1639 vaccinated group, that group was swabbed again at day 14 to evaluate viral load and potential vaccine rolling. This data can be seen in FIG. 7. Both percent positive (~85%) and viral load (mean Ct of 25.5) increased in the DE1639 vaccinated group at day 14 compared to day 7. This would indicate that the peak of viral vaccine replication is occurring much later for this vaccine than traditional IBV vaccines. The DE1639 vaccine group was also swabbed at 28 dpv to see how much vaccine was still present (FIG. 8). ~25% of the birds were still positive, with viral loads ranging from Ct values of 36-22 (mean Ct ~28). This shows that vaccine is continuing to roll in the flock.

Ten chickens in each vaccine group were randomly selected and challenged at 28 days post vaccination with a pathogenic DMV/1639 type IB virus at $1\times10^4$ $EID_{50}$ per bird. Five days post challenge, clinical respiratory signs were recorded, and swabs were taken for IBV load analysis by PCR. All groups had statistically significantly lower clinical signs than the non-vaccinated, DMV/1639 challenged group (FIG. 9).

Viral loads as determined by DMV/1639 type specific PCR showed that all groups had statistically significantly lower viral loads than the non-vaccinated, challenged group (FIG. 10). Overall, the mean Ct value of the non-vaccinated, challenged group was ~23, and all 5 samples were very close to this value. The group vaccinated with the DE1639 vaccine had 8/10 samples positive for virus after challenge, but the samples broke into two distinct groups. One group clustered around the 29 Ct value mark and the other group clustered around the 34 Ct value mark. Since this assay cannot differentiate vaccine from challenge virus, it is impossible to say that all or none of these positive samples are vaccine or challenge. But based on the day 28 samples from this group and experience when performing these studies, it can be estimated that half of these positive values are from challenge virus. The PDRC DMV/1639 vaccinated group only had one positive sample post challenge, with a Ct value of ~33, indicating little virus present. This test shows that the PDRC vaccine was fully protective against this challenge virus based on 9-CFR standards (90% or >samples were negative for virus).

Discussion

The experiment concluded as expected. The DE1639 vaccine did not fully infect at the time of initial vaccination, and then lingered in the birds until at least the challenge timepoint. Furthermore, virus was detected post-challenge at a rate higher than vaccine was detected prior to challenge, indicating that at least some of the virus detected after challenge was challenge virus. This means either the DE1639 vaccine is not a perfect antigenic match to the challenge, or the birds that did not get vaccinated due to the poor infection rate were not protected from the challenge. Either way, this vaccine was not effective at stopping the challenge virus. This matches the field situation as well, where DMV/1639 is continually detected in flocks that are vaccinated using the autogenous DMV vaccine. The only group that was fully protected (90% or >were negative) was the group vaccinated with the heat attenuated PDRC DMV/1639 vaccine described herein (deposited with the ATCC® Patent Depository as Patent Deposit Number PTA-126757). The PDRC DMV/1639 vaccine was developed from a recent 2019 isolate and it appears to be a good antigenic match to the field virus. Also, this vaccine was given at a lower titer than the other vaccines ($1\times100^{3.4}$ $EID_{50}$) but still had near perfect infection and replication dynamics.

One possible explanation for the improved efficacy of the newer PDRC vaccine is that it is a better antigenic match to the currently circulating field viruses. In the phylogenetic table shown in FIG. 11, different isolates of the DMV/1639 virus are compared. The lower box represents isolates from the original 2015 outbreak, with the autogenous vaccine indicated with the arrow. The more recent isolates from 2019 are in the upper box, with the PDRC vaccine indicated by the arrow. The sequence of the challenge virus used in this study isolated from a broiler flock in DelMarVa falls in the clade shown by the upper box as well. It seems as though the virus has evolved as it has moved around the country but has begun to "settle" as most isolates now group together.

Example 4

Back-Passage of the Heat Attenuated PDRC DMV/1639 Vaccine to Evaluate Attenuation Stability With this example, the stability of the heat attenuated PDRC DMV/1639 vaccine as described herein was evaluated by back-passage of the vaccine in susceptible chickens.

Materials and Methods

Virus. The attenuated (by heat treatment) PDRC DMV/1639 virus vaccine deposited at the ATCC under Patent Designation PTA-126757 was used in this study.

Experimental Design. One-day old specific pathogen free (SPF) chicks were used for this experiment. Five 1-day old chicks were initially given $3.16 \times 10^3$ 50% embryo infectious doses ($EID_{50}$) of vaccine intranasally and intraocularly in a 0.1 ml volume. After either 2- or 3-days post-vaccination, the choanal cleft of each bird was swabbed, pooled into 3 mls of PBS (pH 7.4) and 0.1 ml of that pooled sample was given to each bird in another group of five 1-day old SPF chicks. This was repeated 10 times. All of the birds were examined for clinical signs throughout the study and, at the last back-passage (back-passage number 10) the five individual birds were necropsied at 5 days post-vaccination. At this necropsy, intrachoanal swabs were taken and not pooled, and the birds were examined for clinical signs and lesions.

Clinical Signs. Clinical signs were recorded and scored based on published laboratory scoring methods (Jackwood et al. *Avian Dis* 59, 368-374 (2015)), where a 0=no signs, 1=slight wheezing or snicking, 2=more pronounced wheezing, sinus exudate, conjunctivitis, and 3=rales.

RNA extraction and virus detection by real time RT-PCR. Intrachoanal swabs from the oropharyngeal area in the palatine cleft were collected and for back-passage groups 1 to 9, they were pooled into 3 mls of ice cold PBS for virus detection by real time RT-PCR. Intrachoanal swabs from five birds in back-passage group 10 were kept as individual samples and placed into 1 ml of ice cold PBS for virus detection by real time RT-PCR.

Viral RNA was extracted from 50 ul of the PBS using the MagMAX-96 RNA Isolation Kit (Ambion Inc., Austin Tex.) according to the manufacturer's protocol on a KingFisher magnetic particle processor (Thermo Scientific, Waltham, MA). Real time RT-PCR was conducted using an Applied Biosystems 7500 Fast Real-Time PCR System (Life Technologies, Carlsbad, CA) and the AGPATH-ID™ One-Step RT-PCR kit (Ambion Inc.) according to the manufacturer's recommendations. Primers and probe for the real time RT-PCR correspond to the specific DMV/1639 serotype. The primers were obtained from Integrated DNA Technologies (Coralville, IA) and Taqman probe was synthesized by BioSearch Technologies (Novato, CA).

Results

None of the birds given the heat attenuated PDRC DMV/1639 vaccine developed clinical signs. In addition, all five birds in the back-passage 10 group were absent of clinical signs and lesions.

Real time RT-PCR results are presented in Table 5. Vaccine virus was detected in all of the pooled samples from back-passage groups 1 to 9 and from each of the individual samples taken from the five birds in pack-passage group 10.

TABLE 5

Real time RT-PCR data for pooled (groups 1-9) and individual (group 10) intrachoanal swab samples.
Discussion

| Back-passage Group[a] | CT[b] value |
| --- | --- |
| 1 | 17.06 |
| 2 | 20.08 |
| 3 | 21.99 |
| 4 | 21.53 |
| 5 | 20.42 |
| 6 | 22.90 |
| 7 | 22.97 |
| 8 | 20.75 |
| 9 | 22.20 |
| 10-1 | 20.80 |
| 10-2 | 21.97 |
| 10-3 | 20.45 |
| 10-4 | 21.32 |
| 10-5 | 21.51 |

[a]Groups 1 through 9 were pools of 5 swabs in 3 ml of PBS and group 10-1 to 10-5 were 5 individual samples in 1 ml of PBS from five birds in the last back-passage group.
[b]CT = cycle threshold Based on the data from this experiment, the heat attenuated PDRC DMV/1639 vaccine was stable in susceptible SPF chickens following 10 back-passages. Vaccine virus was detected in chicks from each of the back-passage groups and no clinical signs in any of the birds or lesions (back-passage group 10 only) were detected. The CT values ranged from 22.97 to 17.06 indicating that a significant amount of vaccine was passaged to each group of chicks. Given that data and the fact that no clinical signs or lesions were seen in the birds clearly indicates that the attenuated nature of the PDRC DMV/1639 vaccine is stable and ought to be safe to use in the field.

Example 5

Purity

The analysis of a sample of the PDRC DMV/1639 vaccine as deposited at the ATCC under Patent Designation PTA-126757 the by the University of Delaware Agricultural and Natural Resources Laboratory for Infectious *Coryza*, Infectious Laryngotracheitis Virus, *Mycoplasma gallisepticum, Mycoplasma synoviae*, NAHLN avian influenza (AIV), NAHLN Avian Paramyxovirus, Infectious Bronchitis Virus (IBV), IBV-DE072/GA99, IBV-Ark, IBV-Mass/Conn, IBV-DMV/1639, and IBV-GA08 detected only IBV and IBV-DMV1639, indicating purity. This analysis was performed to ensure that the isolate contained no pathogen commonly found in commercial poultry, or any pathogen that could be devastating to commercial poultry (such as AI or NDV). When considerations are being made for vaccine production, this purity is of the utmost importance and should be thoroughly evaluated. This analysis was also performed to ensure that any results obtained from testing (see previous examples) were not influenced, either positively or negatively, by a confounding variable such as contamination with another pathogen. These data ensure that the highest quality control care was taken when isolating, propagating, and preparing the vaccine seed, and that the data presented are a true reflection of this DMV/1639/11 virus vaccine alone.

Example 6

Field Studies

The PDRC DMV/1639 vaccine as described here in (deposited at the ATCC under Patent Designation PTA-126757) has been administered to over 50 million chickens in commercial settings. Analysis of vaccine takes show that the vaccine is very effective at infecting and replicating in commercial conditions. This analysis is critical for ensuring vaccine success as most poultry vaccines against infectious bronchitis virus (like the DMV/1639 vaccine described herein) are tested and validated using an eyedrop administration method. While the gold standard for laboratory experiments, it is impossible to eyedrop vaccinate every commercial chicken produced. For this reason, commercial chickens are vaccinated en mass, using a spray cabinet that aerosolizes vaccine onto the chicks. There are many potential points of failure in this process that have influenced vaccine efficacy for other IBV vaccines in the past. This data shows that, even when mass applied by spray, the DMV/1639 vaccine described herein is very effective at infecting and replicating chickens, which is the primary step in inducing a proper immune response. This data also aids in determining the most efficacious dose of the vaccine, as adverse vaccine reactions and actual dose given to chicks can be recorded and evaluated in the commercial setting in which the vaccine will be used.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. An infectious bronchitis virus (IBV) isolate, wherein the IBV isolate comprises the heat attenuated IBV isolate PDRC DMV/1639 deposited at the ATCC under Patent Designation PTA-126757.

2. The IBV isolate of claim 1, wherein the IBV isolate is lyophilized, freeze dried, or frozen.

3. A composition comprising the IBV isolate of claim 1.

4. The composition of claim 3 further comprising a pharmaceutically acceptable carrier.

5. A vaccine comprising the isolated IBV isolate of claim 1.

6. A vaccine for birds of the order Galliformes comprising a titer of about $10^{1.5}$ to about $10^{10}$ $EID_{50}$ (embryo infective dose)/ml of the heat attenuated IBV isolate PDRC DMV/1639 deposited at the ATCC under Patent Designation PTA-126757.

7. The vaccine of claim 5, further comprising an adjuvant.

8. The vaccine of claim 5, further comprising other viral material.

9. The vaccine of claim 5, wherein the composition or formulation is formulated for intranasal, intraocular, oral, mucosal, intramuscular, subcutaneous, or in ovo administration.

10. The vaccine of claim 5, wherein the composition or vaccine is formulated for spraying or aerosolizing.

11. An effervescent tablet comprising an IBV isolate thereof of claim 1.

12. A method:
of producing an immune response to an infectious bronchitis virus (IBV) in poultry,
of reducing one or more clinical signs and/or viral load induced by an infectious bronchitis virus (IBV) infection in poultry,
for reducing susceptibility of a bird of the order Galliformes against infectious bronchitis virus (IBV) infection, and/or
for protecting a bird of the order Galliformes against infectious bronchitis virus (IBV) infection,
the method comprising administering to the bird an effective amount of the IBV isolate of claim 1.

13. The method of claim 12, wherein administration is intranasal, intraocular, oral, mucosal, intramuscular, or subcutaneous.

14. The method of claim 12, wherein administration comprises in ovo administration.

15. The method of claim 12, wherein the IBV isolate is administered by aerosol.

16. The method of claim 12, wherein the IBV isolate is administered by drinking water.

17. The method of claim 12, wherein administration comprises administration to a breeder hen.

18. The method of claim 12, wherein the poultry comprises a bird of the order Galliformes.

19. The method of claim 12, wherein the bird is a chicken or turkey.

* * * * *